United States Patent

Lunkenheimer et al.

Patent Number: 5,877,195
Date of Patent: *Mar. 2, 1999

[54] 2-PERHALOGENALKYL-SUBSTITUTED BENZIMIDAZOLES, AND THEIR USE AS PESTICIDES

[75] Inventors: Winfried Lunkenheimer, Wuppertal; Bernd Baasner, Bergisch Gladbach; Folker Lieb, Leverkusen; Christoph Erdelen; Jügen Hartwig, both of Leichlingen; Ulrike Wachendorff-Neumann, Bonn; Wilhelm Stendel, Wuppertal; Ulrich Gorgens, Ratingen, all of Germany

[73] Assignee: Bayer Aktiengesellschaft, Leverkusen, Germany

[ * ] Notice: The term of this patent shall not extend beyond the expiration date of Pat. No. 5,656,649.

[21] Appl. No.: 749,434

[22] Filed: Nov. 15, 1996

Related U.S. Application Data

[63] Continuation of Ser. No. 424,339, filed as PCT/EP93/02948 Oct. 25, 1993, abandoned.

[30] Foreign Application Priority Data

Nov. 6, 1992 [DE] Germany .......... 42 37 548.7

[51] Int. Cl.$^6$ .......... A01N 43/52; C07D 235/10
[52] U.S. Cl. .......... 514/394; 548/309.7; 548/310.1; 548/310.4
[58] Field of Search .......... 548/309.7, 310.1, 548/310.4; 514/394

[56] References Cited

U.S. PATENT DOCUMENTS 5,306,692 4/1994 Baron et al. .......... 504/139

5,656,649 8/1997 Lunkenheimer .......... 514/394

FOREIGN PATENT DOCUMENTS 1213796 4/1967 United Kingdom.

Primary Examiner—Patricia L. Morris
Attorney, Agent, or Firm—Sprung Kramer Schaefer & Briscoe

[57] ABSTRACT

The invention relates to new substituted benzimidazoles of the general formula (I)

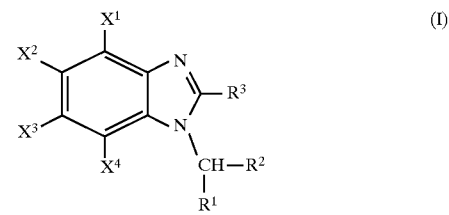

in which $R^1$ represents hydrogen, alkyl or optionally substituted aryl, $R^2$ represents hydroxyl, cyano, alkoxy or optionally substituted amino, $R^3$ represents perhalogenoalkyl, and $X^1$, $X^2$, $X^3$ and $X^4$, independently of one another, in each case represent hydrogen, halogen, nitro or optionally substituted aryloxy, but with at least one of the substituents $X^1$, $X^2$, $X^3$ or $X^4$ being different from hydrogen, with the exception of the compound 1-cyanomethyl-2-trifluoromethyl-5,6-dichlorbenzimidazole, to their preparation and to their use as agents for combating pests.

3 Claims, No Drawings

2-PERHALOGENALKYL-SUBSTITUTED BENZIMIDAZOLES, AND THEIR USE AS PESTICIDES

This application is a continuation of application Ser. No. 08/424,339 now abandoned, which is 371 of PCT/EP93/02948, filed Oct. 25, 1993, filed on Apr. 25, 1995 which is pending.

The invention relates to new substituted benzimidazoles, to a number of processes for their preparation and their use as agents for combating pests.

It is known that certain phosphoric acid esters or carbamates, such as, for example, the compound O,S-dimethyl-thiolo-phosphoric acid amide or the compound N-methyl-O-(2-isopropoxyphenyl)-carbamate possess insecticidal properties (cf. e.g. DE-12 10 835 or DE 11 08 202).

However, the extent and/or duration of the action of these previously known compounds, especially on certain insects or at low application concentrations, is not completely satisfactory in all areas of application.

New substituted benzimidazoles of the general formula (I)

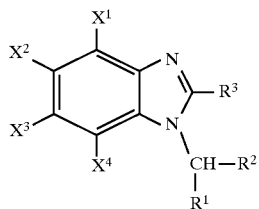

have now been found,
in which
$R^1$ represents hydrogen, alkyl or optionally substituted aryl,
$R^2$ represents hydroxyl, cyano, alkoxy or optionally substituted amino,
$R^3$ represents perhalogenoalkyl, and
$X^1$, $X^2$, $X^3$ and $X^4$, independently of one another, in each case represent hydrogen, halogen, nitro or optionally substituted aryloxy, but with at least one of the substituents $X^1$, $X^2$, $X^3$ or $X^4$ being different from hydrogen,
with the exception of the compound 1-cyanomethyl-2-trifluoromethyl-5,6-dichlorbenzimidazole.

The compounds of the formula (I) may if appropriate, depending on the nature and number of the substituents, be present as geometric and/or optical isomers or regioisomers, or their isomer mixtures in varying composition. Both the pure isomers and the isomer mixtures are claimed according to the invention.

It has also been found that the new substituted benzimidazoles of the general formula (I)

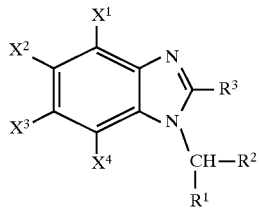

in which
$R^1$ represents hydrogen, alkyl or optionally substituted aryl,
$R^2$ represents hydroxyl, cyano, alkoxy or optionally substituted amino,
$R^3$ represents perhalogenoalkyl, and
$X^1$, $X^2$, $X^3$ and $X^4$, independently of one another, in each case represent hydrogen, halogen, nitro or optionally substituted aryloxy, but with at least one of the substituents $X^1$, $X^2$, $X^3$ or $X^4$ being different from hydrogen,
with the exception of the compound 1-cyanomethyl-2-trifluoromethyl-5,6-dichlorbenzimidazole,
are obtained if 1H-benzimidazoles of the formula (II)

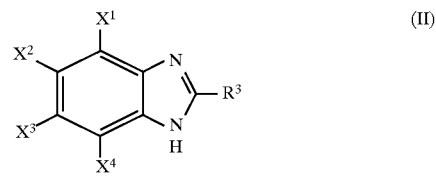

in which
$R^3$, $X^1$, $X^2$, $X^3$ and $X^4$ have the meaning given above,
are reacted with compounds of the formula (III)

in which
A represents a suitable leaving group,
$R^1$ has the meaning given above and
$R^2$ has the meaning given above
optionally in the presence of a diluent and optionally in the presence of a reaction auxiliary.

Finally, it has been found that the new substituted benzimidazoles of the general formula (I) possess a good activity against pests.

Surprisingly, the substituted benzimidazoles of the general formula (I) according to the invention exhibit a considerably improved insecticidal activity in comparison to the phosphoric acid esters or carbamates known from the prior art, such as, for example, the compound O,S-dimethyl-thiolo-phosphoric acid amide or the compound N-methyl-O-(2-isopropoxyphenyl)-carbamate, which are closely related compounds in terms of their action.

A general definition of the substituted benzimidazoles according to the invention is given by the formula (I). Preferred compounds of the formula (I) are those in which
$R^1$ represents hydrogen, straight-chain or branched alkyl having 1 to 8 carbon atoms or phenyl which is optionally substituted once or more than once by identical or different substituents, possible substituents being:
halogen, cyano, nitro, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl having in each case 1 to 6 carbon atoms in the individual alkyl moieties, divalent dioxyalkylene having 1 to 5 carbon atoms which is optionally substituted once or more than once by identical or different substituents comprising halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally substituted once or more than once by identical or different substituents comprising halogen and/or straight-chain or branched alkyl having 1 to 6 carbon atoms and/or straight-chain or branched halogenoalkyl having 1 to 6 carbon atoms and 1 to 13 identical or different halogen atoms, $R^2$ represents hydroxyl, cyano, alkoxy having 1 to 8 carbon atoms or amino which is optionally substituted once or twice by identical or different substituents, possible substituents being:

straight-chain or branched alkyl having 1 to 8 carbon atoms, straight-chain or branched alkenyl having 2 to 8 carbon atoms, cycloalkyl having 3 to 8 carbon atoms, alkoxycarbonyl, alkylthio-carbonyl, alkoxythiocarbonyl or alkylthio-thiocarbonyl having in each case 1 to 8 carbon atoms in the individual straight-chain or branched alkyl moieties, a divalent closed alkanediyloxycarbonyl ring having 2 to 6 carbon atoms in the alkanediyl moiety, or arylalkyl or aryl having in each case 6 to 10 carbon atoms in the aryl moiety and optionally 1 to 6 carbon atoms in the straight-chain or branched alkyl moiety, each of which is optionally substituted once or more than once by identical or different substituents, possible substituents of aryl in each case being those mentioned for $R^1$, $R^3$ represents straight-chain or branched perhalogenoalkyl having 1 to 8 carbon atoms and 1 to 17 identical or different halogen atoms, and $X^1$, $X^2$, $X^3$ and $X^4$, independently of one another, in each case represent hydrogen, fluorine, chlorine, bromine, iodine, nitro or aryloxy having 6 to 10 carbon atoms in the aryl moiety which is optionally substituted in the aryl moiety once or more than once by identical or different substituents, possible substituents of aryl being those mentioned for $R^1$, but with at least one of the substituents $X^1$, $X^2$, $X^3$ or $X^4$ being different from hydrogen, and with the exception of the compound 1-cyanomethyl-2-trifluoromethyl-5,6-dichlorobenzimidazole.

Particularly preferred compounds of the formula (I) are those in which $R^1$ represents hydrogen, straight-chain or branched alkyl having 1 to 6 carbon atoms or phenyl which is optionally substituted once to three times by identical or different substituents, possible substituents being:

halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl having in each case 1 to 4 carbon atoms in the individual alkyl moities, divalent dioxyalkylene having 1 to 4 carbon atoms which is optionally substituted once to six times by identical or different substituents comprising halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally substituted once to five times by identical or different substituents comprising halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydroxyl, cyano, alkoxy having 1 to 6 carbon atoms or amino which is optionally substituted once or twice by identical or different substituents, possible substituents being:

straight-chain or branched alkyl having 1 to 6 carbon atoms, straight-chain or branched alkenyl having 2 to 6 carbon atoms, cycloalkyl having 3 to 7 carbon atoms, alkoxycarbonyl, alkylthio-carbonyl, alkoxythiocarbonyl or alkylthio-thiocarbonyl having in each case 1 to 6 carbon atoms in the individual straight-chain or branched alkyl moieties, a divalent closed alkanediyloxycarbonyl ring having 2 to 5 carbon atoms in the alkanediyl moiety, or arylalkyl or aryl having in each case 6 or 10 carbon atoms in the aryl moiety and optionally 1 to 6 carbon atoms in the straight-chain or branched alkyl moiety, each of which is optionally substituted once to five times by identical or different substituents, possible substituents of aryl being those mentioned for $R^1$, $R^3$ represents straight-chain or branched perhalogenoalkyl having 1 to 6 carbon atoms and 1 to 13 identical or different halogen atoms, and $X^1$, $X^2$, $X^3$ and $X^4$, independently of one another, in each case represent hydrogen, fluorine, chlorine, bromine, iodine, nitro or aryloxy having 6 or 10 carbon atoms in the aryl moiety, which is optionally substituted once to five times by identical or different substituents, possible substituents of aryl being those mentioned for $R^1$, but with at least one of the substituents $X^1$, $X^2$, $X^3$ or $X^4$ being different from hydrogen, with the exception of the compound 1-(cyanomethyl-2-trifluoromethyl-5,6-dichlorobenzimidazole. Preferred aryl radicals which can be mentioned are phenyl and naphthyl.

Compounds of the formula (I) which are very particularly preferred are those in which $R^1$ represents hydrogen, straight-chain or branched alkyl having 1 to 4 carbon atoms or phenyl which is optionally substituted once or twice by identical or different substituents, possible substituents being:

halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoximinoalkyl having in each case 1 to 3 carbon atoms in the individual alkyl moieties, divalent dioxyalkylene having 1 to 3 carbon atoms which is optionally substituted once to four times by identical or different substituents comprising halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally substituted once to three times by identical or different substituents comprising halogen and/or straight-chain or branched alkyl having 1 to 3 carbon atoms and/or straight-chain or branched halogenoalkyl having 1 to 3 carbon atoms and 1 to 7 identical or different halogen atoms, $R^2$ represents hydroxyl, cyano, alkoxy having 1 to 6 carbon atoms or amino which is optionally substituted once or twice by identical or different substituents, possible substituents being:

straight-chain or branched alkyl having 1 to 4 carbon atoms, straight-chain or branched alkenyl having 2 to 4 carbon atoms, cycloalkyl having 3 to 6 carbon atoms, alkoxycarbonyl, alkylthio-carbonyl, alkoxythiocarbonyl or alkylthio-thiocarbonyl having in each case 1 to 4 carbon atoms in the individual straight-chain or branched alkyl moieties, a divalent closed alkanediyloxycarbonyl ring having 2 to 4 carbon atoms in the alkanediyl moiety, or phenylalkyl or phenyl having optionally 1 to 3 carbon atoms in the straight-chain or branched alkyl moiety, each of which is optionally substituted once or twice by identical or different substituents, possible substituents of phenyl in each case being those mentioned for $R^1$, $R^3$ represents straight-chain or branched perhalogenoalkyl having 1 to 4 carbon atoms and 1 to 9 identical or different halogen atoms, or cyano, and $X^1$, $X^2$, $X^3$ and $X^4$, independently of one another, in each case represent hydrogen, chlorine, bromine, nitro or phenyloxy which is optionally substituted in the phenyl moiety up to three times by identical or different substituents, possible substituents of phenyl being those mentioned for $R^1$, but with at least one of the substituents $X^1$, $X^2$, $X^3$ or $X^4$ being different from hydrogen, with the exception of the compound 1-cyanomethyl-2-trifluoromethyl-5,6-dichlorobenzimidazole.

Apart from the compounds mentioned in the Preparation Examples, the following individual substituted benzimidazoles of the general formula (I) may be mentioned:

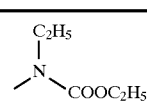

| $X^1$ | $X^2$ | $X^3$ | $X^4$ | $R^1$ | $R^2$ | $R^3$ |
|---|---|---|---|---|---|---|
| Br | H | Cl | H | H | 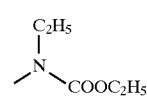 | $CF_3$ |
| Br | H | Br | H | H | 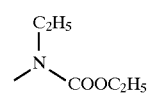 | $CF_3$ |
| Br | H | $NO_2$ | H | H | 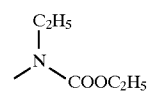 | $CF_3$ |
| Cl | H | Cl | H | H | 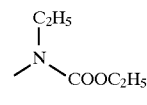 | $CF_3$ |
| Cl | H | Br | H | H | 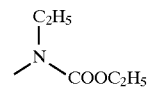 | $CF_3$ |
| H | H | $NO_2$ | H | H | 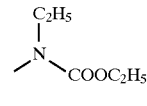 | $CF_3$ |
| Br | H | $C_6H_5O$ | H | H | 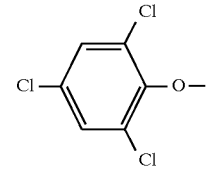 | $CF_3$ |
| Cl | H | (2,4,6-trichlorophenoxy) | H | H | (N(C_2H_5)COOC_2H_5) | $CF_3$ |

-continued
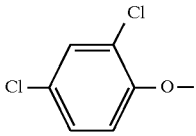
| $X^1$ | $X^2$ | $X^3$ | $X^4$ | $R^1$ | $R^2$ | $R^3$ |
|---|---|---|---|---|---|---|
| Cl | H | 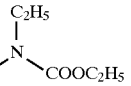 | H | H | 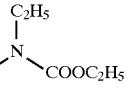 | $CF_3$ |
| Br | H | Cl | H | H | 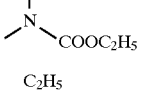 | $C_2F_5$ |
| Br | H | Br | H | H | 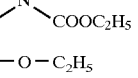 | $C_2F_5$ |
| H | Cl | Cl | H | H | 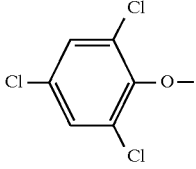 | $C_2F_5$ |
| Cl | H | 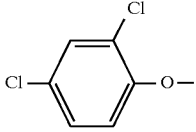 | H | H | $-O-C_2H_5$ | $CF_3$ |
| Cl | H | 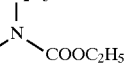 | H | H | $-O-C_2H_5$ | $CF_3$ |
| Br | H | Cl | H | H | 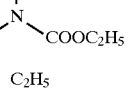 | $C_2F_5$ |
| Br | H | Br | H | H | 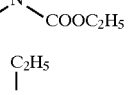 | $C_2F_5$ |
| H | Cl | Cl | H | H | 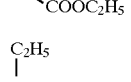 | $C_2F_5$ |
| Br | H | $NO_2$ | H | H | 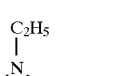 | $C_2F_5$ |
| Cl | H | Cl | H | H |  | $C_2F_5$ |
| Cl | H | Br | H | H |  | $C_2F_5$ |

-continued

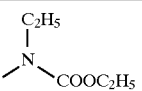

(I)

| X¹ | X² | X³ | X⁴ | R¹ | R² | R³ |
|---|---|---|---|---|---|---|
| H | H | NO₂ | H | H | $\begin{array}{c}C_2H_5\\|\\N\\\diagdown COOC_2H_5\end{array}$ | C₂F₅ |
| Br | H | C₆H₅O | H | H | $\begin{array}{c}C_2H_5\\|\\N\\\diagdown COOC_2H_5\end{array}$ | C₂F₅ |
| Cl | H | 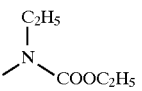 | H | H | $\begin{array}{c}C_2H_5\\|\\N\\\diagdown COOC_2H_5\end{array}$ | C₂F₅ |
| Cl | H | 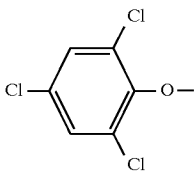 | H | H | $\begin{array}{c}C_2H_5\\|\\N\\\diagdown COOC_2H_5\end{array}$ | C₂F₅ |
| Br | H | Cl | H | H | —O—C₂H₅ | C₂F₅ |
| Br | H | Br | H | H | —O—C₂H₅ | C₂F₅ |
| H | Cl | Cl | H | H | —O—C₂H₅ | C₂F₅ |
| Br | H | NO₂ | H | H | —O—C₂H₅ | C₂F₅ |
| Cl | H | Cl | H | H | —O—C₂H₅ | C₂F₅ |
| Cl | H | Br | H | H | —O—C₂H₅ | C₂F₅ |
| H | H | NO₂ | H | H | —O—C₂H₅ | C₂F₅ |
| Br | H | C₆H₅O | H | H | —O—C₂H₅ | C₂F₅ |
| Cl | H | 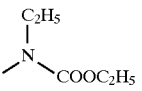 | H | H | —O—C₂H₅ | C₂H₅ |
| Cl | H | 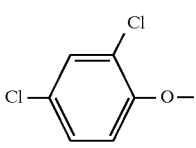 | H | H | —O—C₂H₅ | C₂F₅ |
| Br | H | Cl | H | H | $\begin{array}{c}C_2H_5\\|\\N\\\diagdown COOC_2H_5\end{array}$ | n-C₃F₇ |
| Br | H | Br | H | H | $\begin{array}{c}C_2H_5\\|\\N\\\diagdown COOC_2H_5\end{array}$ | n-C₃F₇ |
| H | Cl | Cl | H | H | $\begin{array}{c}C_2H_5\\|\\N\\\diagdown COOC_2H_5\end{array}$ | n-C₃F₇ |

-continued
| X¹ | X² | X³ | X⁴ | R¹ | R² | R³ |
|---|---|---|---|---|---|---|
| Br | H | $NO_2$ | H | H | 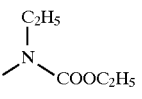 | n-$C_3F_7$ |
| Cl | H | Cl | H | H | 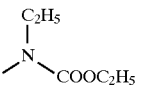 | n-$C_3F_7$ |
| Cl | H | Br | H | H | 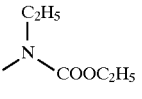 | n-$C_3F_7$ |
| H | H | $NO_2$ | H | H | 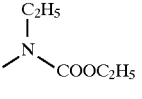 | n-$C_3F_7$ |
| Br | H | $C_6H_5O$ | H | H | 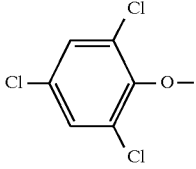 | n-$C_3F_7$ |
| Cl | H | 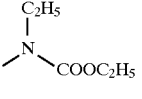 | H | H | 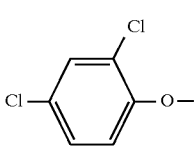 | n-$C_3F_7$ |
| Cl | H | 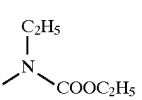 | H | H | 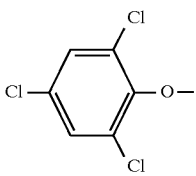 | n-$C_3F_7$ |
| Br | H | Cl | H | H | $-O-C_2H_5$ | n-$C_3F_7$ |
| Br | H | Br | H | H | $-O-C_2H_5$ | n-$C_3F_7$ |
| H | Cl | Cl | H | H | $-O-C_2H_5$ | n-$C_3F_7$ |
| Br | H | $NO_2$ | H | H | $-O-C_2H_5$ | n-$C_3F_7$ |
| Cl | H | Cl | H | H | $-O-C_2H_5$ | n-$C_3F_7$ |
| Cl | H | Br | H | H | $-O-C_2H_5$ | n-$C_3F_7$ |
| H | H | $NO_2$ | H | H | $-O-C_2H_5$ | n-$C_3F_7$ |
| Br | H | $C_6H_5O$ | H | H | $-O-C_2H_5$ | n-$C_3F_7$ |
| Cl | H | 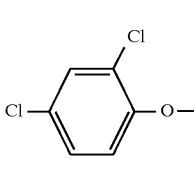 | H | H | $-O-C_2H_5$ | n-$C_3F_7$ |
| Cl | H |  | H | H | $-O-C_2H_5$ | n-$C_3F_7$ |

-continued $$\text{(I)}$$

Structure: benzimidazole with X¹ at 4-position, X² at 5-position, X³ at 6-position, X⁴ at 7-position; N1-CH(R¹)(R²); C2-R³.

| X¹ | X² | X³ | X⁴ | R¹ | R² | R³ |
|----|----|----|----|----|----|----|
| Cl | H | 2,6-dichloro-4-(trifluoromethyl)phenoxy | H | H | —O—C₂H₅ | CF₃ |
| Cl | H | 2,6-dichloro-4-(trifluoromethyl)phenoxy | H | H | —O—C₂H₅ | C₂F₅ |
| Cl | H | 2,6-dichloro-4-(trifluoromethyl)phenoxy | H | H | —O—C₂H₅ | n-C₃F₇ |
| Cl | H | 2,6-dichloro-4-(trifluoromethyl)phenoxy | H | H | —N(C₂H₅)(COOC₂H₅) | CF₃ |
| Cl | H | 2,6-dichloro-4-(trifluoromethyl)phenoxy | H | H | —N(C₂H₅)(COOC₂H₅) | C₂F₅ |
| Cl | H | 2,6-dichloro-4-(trifluoromethyl)phenoxy | H | H | —N(C₂H₅)(COOC₂H₅) | n-C₃F₇ |
| Cl | H | Cl | H | H | —O—C₂H₅ | n-C₇H₁₅ |
| H | Cl | Cl | H | H | —O—C₂H₅ | n-C₇H₁₅ |
| Cl | H | Cl | H | H | —N(C₂H₅)(COOC₂H₅) | n-C₇H₁₅ |
| H | Cl | Cl | H | H | —N(C₂H₅)(COOC₂H₅) | n-C₇H₁₅ |

-continued

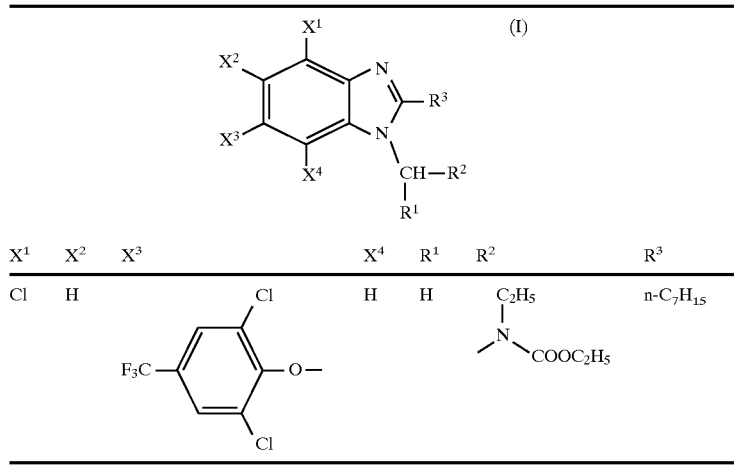

Using, for example, 5,6-dichloro-2-trifluoromethyl-benzimidazole and chloromethyl ethyl ether as starting compounds, the course of the reaction of the process according to the invention can be represented by the following formula scheme:

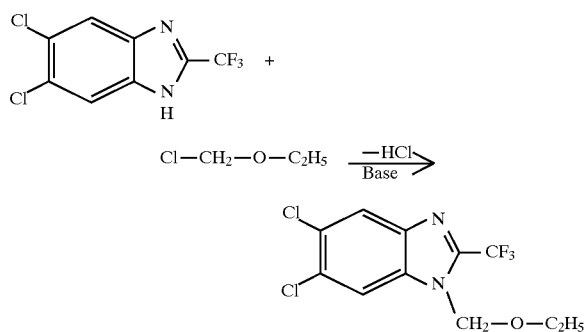

general definition of the 1H-benzimidazoles required as starting substances for carrying out the process according to the invention is given by the formula (II). In this formula (II), $R^3$, $X^1$, $X^2$, $X^3$ and $X^4$ preferably represent those radicals which have already been mentioned as preferred for these substituents in connection with the description of the compounds of the formula (I) according to the invention.

The 1H-benzimidazoles of the formula (II) are known or can be obtained by analogy with known processes (cf. e.g. J. Amer. Chem. Soc. 75, 1292 [1953]; U.S. Pat. No. 3,576,818).

A general definition of the compounds additionally required as starting materials for carrying out the process according to the invention is given by the formula (III). In this formula (III), $R^1$ and $R^2$ preferably represent those radicals which have already been mentioned as preferred for these substituents in connection with the description of the substances of the formula (I) according to the invention.

A preferably represents a leaving radical which is usual in alkylating agents, preferably halogen and in particular chlorine, bromine or iodine, or represents in each case optionally substituted alkylsulphonyloxy, alkoxysulphonyloxy or arylsulphonyloxy, such as, in particular, methanesulphonyloxy, trifluoromethanesulphonyloxy, methoxysulphonyloxy, ethoxysulphonyloxy or p-toluenesulphonyloxy.

In addition, A also represents an alcohol, alkanoyloxy or alkoxy group, such as, for example, a hydroxyl, acetoxy or methoxy group if the intention is to use the process according to the invention to prepare compounds of the formula (I) in which $R^1$ is different from hydrogen.

The compounds of the formula (III) are known or can be obtained by analogy with known processes (cf. e.g. DE 20 40 175; DE 21 19 518; Synthesis 1973, 703).

Suitable diluents for carrying out the process according to the invention are inert organic solvents. These include, in particular, aliphatic, alicyclic or aromatic, optionally halogenated, hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl or diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, or bases such as pyridine, or organic acids such as formic acid or acetic acid.

The process according to the invention is preferably carried out in the presence of a suitable reaction auxiliary. Suitable such auxiliaries are all conventional inorganic or organic bases. They include, for example, alkaline earth metal or alkali metal hydrides, hydroxides, amides, alcoholates, acetates, carbonates or hydrogen carbonates, such as, for example, sodium hydride, sodium amide, lithium diethylamide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, organolithium compounds such as n-butyllithium, and tertiary amines such as trimethylamine, triethylamine, tributylamine, di-isopropyl-ethylamine, tetramethylguanidine, N,N-dimethylaniline, pyridine, piperidine, N-methylpiperidine, N,N-dimethylaminopyridine, diazobicyclooctane (DABCO), diazobicyclononene (DBN) or diazabicycloundecene (DBU).

In cases where the intention is to use the process according to the invention to prepare compounds of the formula (I) in which $R^1$ is different from hydrogen, suitable reaction auxiliaries also include organic or inorganic acids, such as, for example, sulphuric acid, hydrochloric acid, p-toluenesulphonic acid and perfluorobutanesulphonic acid, or strongly acidic ion exchangers.

The process according to the invention can optionally also be carried out in a two-phase system such as, for example, water/toluene or water/dichloromethane, optionally in the presence of a suitable phase-transfer catalyst. Examples which may be mentioned of such catalysts are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyldimethyl-ammonium methyl sulphate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

When carrying out the process according to the invention, the reaction temperatures can be varied over a relatively wide range. It is in general carried out at temperatures of between −70° C. and +200° C., preferably at temperatures of between 0° C. and 130° C.

The process according to the invention is usually carried out under atmospheric pressure. However, it is also possible to work under increased or reduced pressure.

Carrying out the process according to the invention requires the use, per mole of 1H-benzimidazole of the formula (II), of in general from 1.0 to 5.0 mol, preferably from 1.0 to 2.5 mol, of compound of the formula (III) and optionally from 0.01 to 5.0 mol, preferably from 1.0 to 3.0 mol, of reaction auxiliary.

In a particular embodiment it is also possible first of all, in a prior reaction step, to silylate the 1H-benzimidazoles of the formula (II) using conventional silylation processes, for example with hexamethyldisilazane or trimethylsilyl chloride, optionally in the presence of a suitable catalyst such as, for example, sulphuric acid, trifluoroacetic acid, ammonium sulphate, imidazole or saccharin, at temperatures of between −20° C. and +150° C., and in a subsequent, second step to react the 1-tri-methylsilylbenzimidazoles, which are obtainable in this way, with alkylating agents of the formula (II) in accordance with the process according to the invention. In this case it is of advantage to add tin tetrachloride as a catalyst for the alkylation reaction (cf. e.g. Chem. Heterocycl. Comp. USSR 24, 514 [1988]).

The implementation of the reaction, the working-up and the isolation of the reaction products are carried out by known methods (cf. also in this respect the Preparation Examples).

The purification of the end products of the formula (I) is carried out using conventional methods, for example by column chromatography or by recrystallization.

Characterization is carried out on the basis of the melting point or, in the case of non-crystallizing compounds— especially in the case of regioisomer mixtures—using proton nuclear magnetic resonance spectroscopy ($^1$H-NMR).

The active substances are suitable for combating animal pests, preferably arthropods and nematodes, in particular insects and arachnids, which are encountered in agriculture, in forests, in the protection of stored goods and materials, and in the hygiene sector. They are effective against normally sensitive and resistant species and against all, or individual, developmental stages. The abovementioned pests include:

From the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and Scutigera spec.;

from the order of the Symphyla, for example, *Scutigerella immaculata;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria;* from the order of the Dermaptera, for example, *Forficula auricularia;* from the order of the Isoptera, for example, Reticulitermes spp.;

from the order of the Anoplura, for example, *Phylloxera vastatrix*, Pemphigus spp., *Pediculus humanus corporis*, Haematopinus spp. and Linognathus spp.;

from the order of the Mallophaga, for example, Trichodectes spp. and Damalinea spp.;

from the order of the Thysanoptera, for example, *Hercinothrips femoralis* and *Thrips tabaci;* from the order of the Heteroptera, for example, Eurigaster spp., *Dysdercus intermedius, Piesma quadrata, Cimex lectularius, Rhodnius prolixus* and Triatoma spp.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Caprocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fuimiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica;* from the order of the Hymenoptera, for example, Diprion spp., Hoplocampa spp., Lasius spp., *Monomorium pharaonis* and Vespa spp.;

from the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa;* from the order of the Siphonaptera, for example, *Xenopsylla cheopis* and Ceratophyllus spp.;

from the order of the Arachnida, for example, *Scorpio maurus* and *Latrodectus mactans;* from the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp, Xiphinema spp. and Trichodorus spp.

The active substances according to the invention are active not only against pests in plants, hygiene and stored goods, but also, in the veterinary sector, against animal parasites (ectoparasites and endoparasites) such as ixodic ticks, argasid ticks, scab mites, trombiculid mites, flies (piercing and lapping), parasitizing fly larvae, lice, biting lice, feather lice, fleas and worms which live as endoparasites.

They are effective against normally sensitive and resistant species and strains, and against all parasitizing and nonparasitizing developmental stages of the ecto- and endoparasites.

The active substances according to the invention are notable for a high degree of insecticidal activity.

They can be employed with particularly good success for combating phytopathogenic insects, as, for example, against the larvae of the mustard beetle (*Phaedon cochleariae*) or against the caterpillars of the cabbage moth (*Plutella maculipennis*) or against the tobacco budworm (*Heliothis virescens*), and for combating phytopathogenic mites, as, for example, against the red spider mite (*Tetranychus urticae*) or for combating phytopathogenic nematodes, as, for example, against the nematode species *Globodera rostochiensis*.

In addition, the active substances according to the invention can also be employed for combating pests in hygiene and stored goods, as, for example, against the house-fly (*Musca domestica*) or against cockroach species, such as, for example, *Periplaneta americana*.

Moreover, the active substances according to the invention can be employed with particularly good success for combating pests which live as parasites of warm-blooded creatures, as, for example, against scab mites (*Psoroptes ovis*).

In addition, the active substances according to the invention also possess a fungicidal activity in vitro.

Depending on their particular physical and/or chemical properties, the active substances can be converted into the customary formulations, such as solutions, emulsions, suspensions, powders, foams, pastes, granules, aerosols, natural and synthetic materials impregnated with active substance, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active substances with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and tin.

The formulations in general contain between 0.1 and 95 percent by weight of active substance, preferably between 0.5 and 90%.

The active substances according to the invention can be present in their commercially available formulations and in the use forms prepared from these formulations, as a mixture with other active substances such as insecticides, attractants, sterilizers, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms, etc.

Furthermore, the active substances according to the invention can be present in their commercially available formulations and in the use forms prepared from these formulations as a mixture with synergists. Synergists are compounds which raise the activity of the active substances without the synergist which is added necessarily being active itself.

The active substance content of the use forms prepared from the commercially available formulations can vary within wide ranges. The active substance concentration of the use forms can be from 0.0000001 up to 95 percent by weight of active substance, preferably between 0.0001 and 1 percent by weight.

Application is effected in a customary manner appropriate to the use forms. When used against pests in hygiene and stored goods, the active substances are notable for an outstanding residual action on wood and clay and for a good alkali stability on limed substrates.

The active substances which can be used in accordance with the invention are also suitable for combating insects, mites, ticks etc. in the sector of animal husbandry and cattle rearing, the combating of the pests enabling better results to be achieved, e.g. higher milk yields, greater weight, more attractive coats, longer lifespan etc.

In this sector, the application of the active substances which can be used in accordance with the invention is carried out in a known manner, for example by oral administration in the form of tablets, capsules, drinking formulations or granules, by dermal or external application in the form of, for example, dipping, spraying, pouring on (pour-on or spot-on) and powdering, and by parenteral administration in the form, for example, of injection, and, furthermore, by the feed-through method. In addition, application as a shaped article (collar, ear-tag) is also possible.

The preparation and the use of the active substances according to the invention is evident from the following examples.

PREPARATION EXAMPLES

Example 1

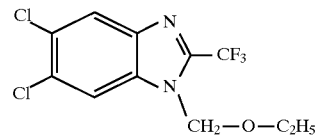

A solution of 14.1 g (0.15 mol) of chloromethyl ethyl ether in 40 ml of ethyl acetate is added dropwise to a mixture of 36 g (0.12 mol) of 5,6-dichloro-2-trifluoromethyl-1H-benzimidazole, 33 g (0.24 mol) of powdered potassium carbonate and 300 ml of ethyl acetate at room temperature, and, after addition is complete, the mixture is heated for a further 4 hours at boiling temperature. For working up, the reaction mixture is cooled and washed twice with 150 ml of water each time, dried over sodium sulphate and concentrated in vacuo. The residue is purified by chromatography on silica gel (eluent: dichloromethane).

32.4 g (83% of theory) of 5,6-dichloro-1-ethoxymethyl-2-trifluoromethyl-benzimidazole are obtained with a melting point of 89°–92° C.

In a corresponding manner and in accordance with the general instructions for the preparation, the following substituted benzimidazoles of the general formula (I) are obtained:

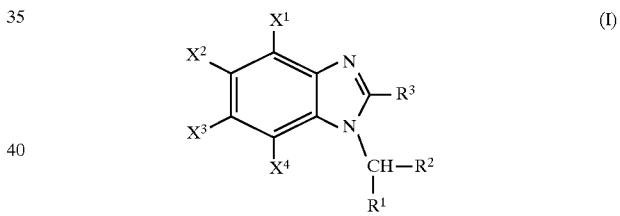

| Ex. No. | X¹ | X² | X³ | X⁴ | R¹ | R² | R³ | physical properties |
|---|---|---|---|---|---|---|---|---|
| 2 | H | Cl | Cl | H | H | CH₃–N(COOCH₃) | CF₃ | m.p. 120–121° C. |
| 3 | H | Cl | Cl | H | H | CH₃–N(COOC₂H₅) | CF₃ | m.p. 95–97° C. |
| 4 | H | Cl | Cl | H | H | C₂H₅–N(COOC₂H₅) | CF₃ | m.p. 104–106° C. |
| 5 | H | Cl | Cl | H | H | C₂H₅–N(COOCH₃) | CF₃ | m.p. 88–89° C. |
| 6 | H | Cl | Cl | H | H | n-C₃H₇–N(COOCH₃) | CF₃ | m.p. 102–103° C. |
| 7 | Cl (H) | H (Cl) | Cl (H) | H (Cl) | H | –O–C₂H₅ | CF₃ | m.p. 57–61° C. (87:13) |
| 8 | Cl (H) | H (Cl) | Cl (H) | H (Cl) | H | CH₃–N(COOCH₃) | CF₃ | m.p. 95–100° C. (92:8) |
| 9 | H | Cl (H) | H (Cl) | H | H | –O–CH(CH₃)₂ | CF₃ | ¹H-NMR*): 5.63; 5.65; 7.35; 7.40; 7.57; 7.78; 7.63; 7.85 |
| 10 | H | Cl (H) | H (Cl) | H | H | CN | CF₃ | ¹H-NMR*): 5.15; 5.18; 7.45; 7.55; 7.83; 7.90 |
| 11 | H | Cl (H) | H (Cl) | H | H | –O–C₂H₅ | CF₃ | ¹H-NMR*): 5.43; 5.48; 7.28–8.01 |
| 12 | H | H (Cl) | Cl (H) | H | H | –O–C₂H₅ | CF₃ | m.p. 75° C. |
| 13 | H | Cl | Cl | H | H | –O–C₂H₅ | CF₃ | m.p. 73° C. |
| 14 | H | Cl (H) | H (Cl) | H | H | CH₃–N(COOC₂H₅) | CF₃ | ¹H-NMR*): 5.88; 5.92; 7.35; 7.67; 7.92 |

-continued

| Ex. No. | $X^1$ | $X^2$ | $X^3$ | $X^4$ | $R^1$ | $R^2$ | $R^3$ | physical properties |
|---|---|---|---|---|---|---|---|---|
| 15 | H | Cl (H) | H (Cl) | H | H | $-N(C_2H_5)-CH_2-COOC_2H_5$ | $CF_3$ | $^1$H-NMR*): 5.88; 5.90; 7.41; 7.79; 7.81 |
| 16 | H | Cl (H) | H (Cl) | H | H | $-N(n-C_3H_7)-CH_2-COOC_2H_5$ | $CF_3$ | $^1$H-NMR*): 5.89; 5.96; 7.37; 7.78; 7.78; 7.81 |
| 17 | H | Cl (H) | H (Cl) | H | H | OH | $CF_3$ |  |
| 18 | H | $NO_2$ (H) | H ($NO_2$) | H | H | $-O-C_2H_5$ | $CF_3$ | $^1$H-NMR*): 7.79–8.78; A: 5.73 B: 5.74 |
| 19 | H | $NO_2$ | H | H | H | $-O-C_2H_5$ | $CF_3$ | m.p.: 48° C. |
| 20 | H | H | $NO_2$ | H | H | $-O-C_2H_5$ | $CF_3$ | m.p.: 90° C. |
| 21 | H | $NO_2$ (H) | H ($NO_2$) | H | H | $-O-n-C_3H_7$ | $CF_3$ | $^1$H-NMR*): 7.80–8.70; A: 5.80 B: 5.85 |
| 22 | H | $NO_2$ (H) | H ($NO_2$) | H | H | $-N(CH_3)-CH_2-COOC_2H_5$ | $CF_3$ | $^1$H-NMR*): 7.95–8.80; A: 5.96 B: 5.99 |
| 23 | H | $NO_2$ (H) | H ($NO_2$) | H | H | $-N(C_2H_5)-CH_2-COOC_2H_5$ | $CF_3$ | $^1$H-NMR*): 7.90–8.75; A: 5.97 B: 5.38 |
| 24 | H | $NO_2$ (H) | H ($NO_2$) | H | H | $-N(n-C_3H_7)-CH_2-COOC_2H_5$ | $CF_3$ | $^1$H-NMR*): 7.91–8.80; A: 5.97 B: 5.99 |
| 25 | H | $NO_2$ (H) | H ($NO_2$) | H | H | OH | $CF_3$ | $^1$H-NMR*): 7.85–8.9; A: 5.85 B: 5.89 |
| 26 | H | F (H) | H (F) | H | H | $-O-C_2H_5$ | $CF_3$ | $^1$H-NMR*): A: 5.63; 7.10–7.90 B: 5.69 |

-continued

| Ex. No. | X¹ | X² | X³ | X⁴ | R¹ | R² | R³ | physical properties |
|---|---|---|---|---|---|---|---|---|
| 27 | H | 2,6-Cl₂-4-CF₃-phenoxy (H) | H | 2,6-Cl₂-4-CF₃-phenoxy | H | —O—C₂H₅ | CF₃ | ¹H-NMR*): 5.61; 5.68; 6.91–7.85 |
| 28 | H | 2,6-Cl₂-4-CF₃-phenoxy (H) | H | 2,6-Cl₂-4-CF₃-phenoxy | H | —O—n-C₃H₇ | CF₃ | ¹H-NMR*): 5.63; 5.79; 6.82–7.86 |
| 29 | H | 2,6-Cl₂-4-CF₃-phenoxy (H) | H | 2,6-Cl₂-4-CF₃-phenoxy | H | N(CH₃)(COOC₂H₅) | CF₃ | ¹H-NMR*): 5.84; 5.86; 6.86–7.90 |
| 30 | H | 2,6-Cl₂-4-CF₃-phenoxy (H) | H | 2,6-Cl₂-4-CF₃-phenoxy | H | N(C₂H₅)(COOC₂H₅) | CF₃ | ¹H-NMR*): 5.80; 5.84; 6.88–7.89 |

-continued

| Ex. No. | X¹ | X² | X³ | X⁴ | R¹ | R² | R³ | physical properties |
|---|---|---|---|---|---|---|---|---|
| 31 | H | ![2,6-dichloro-4-CF3-phenoxy (H)] | ![2,6-dichloro-4-CF3-phenoxy] | H | H | n-$C_3H_7$, $-N-COOC_2H_5$ | $CF_3$ | ¹H-NMR*): 5.78(s), 5.88(s), 6.88–7.95 (m) |
| 32 | H | ![2,6-dichloro-4-CF3-phenoxy (H)] | ![2,6-dichloro-4-CF3-phenoxy] | H | H | CN | $CF_3$ | ¹H-NMR*): 5.11; 6.95; 7.04; 7.74; 7.93 |
| 33 | Br | Cl | Cl | H | H | $C_2H_5$, $-N-COOC_2H_5$ | $CF_3$ | m.p. 100–103° C. |

*)The ¹H-NMR spectra were recorded in deuterochloroform ($CDCl_3$) or hexadeutero-dimethyl sulphoxide (DMSO-$d_6$) using tetramethylsilane (TMS) as the internal standard. The value given is the chemical shift as d in ppm.

Preparation of the Starting Compound

Example II-1

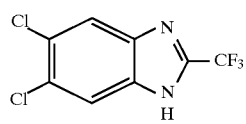

35.4 g (0.2 mol) of 4,5-dichlorophenylene-diamine are heated with 150 ml of trifluoroacetic acid for 3 hours at reflux temperature. For working up, excess trifluoroacetic acid is distilled off and the residue is partitioned between 100 ml of water and 300 ml of ethyl acetate. The organic phase is separated off and washed successively with in each case 100 ml of aqueous sodium hydrogen carbonate solution and water, dried over sodium sulphate and concentrated in vacuo. The residue is purified by chromatography on silica gel (eluent: cyclohexane/ethyl acetate 1:1).

42.1 g (81% of theory) of 5,6-dichloro-2-trifluoromethyl-1H-benzimidazole are obtained with a melting point of 225°–230° C.

In a corresponding manner, the following 1H-benzimidazoles of the formula (II) are obtained:

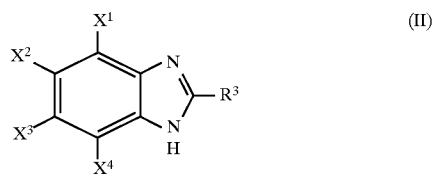

in which
X represents fluorine or chlorine [the individual compounds concerned are chloro-(2-fluoro-1-fluoromethyl-ethoxy)-methane (formula (I), X=fluorine) and chloro-(2-chloro-1-fluoromethyl-ethoxy)-methane (formula (I), X=chlorine)]
are obtainable by reacting halogenated isopropanols of the formula

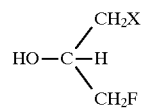

in which
X represents fluorine or chlorine at −20° to +20° C. with formaldehyde and hydrogen chloride.

They are used for the preparation of substituted benzimidazoles of the formula

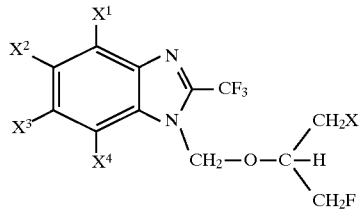

in which
X represents fluorine or chlorine and
$X^1$, $X^2$, $X^3$ and $X^4$, independently of one another, in each case represent hydrogen, halogen, cyano, nitro, in each

| Ex. No. | $X^1$ | $X^1$ | $X^3$ | $X^4$ | $R^3$ | physical properties |
|---|---|---|---|---|---|---|
| II-2 | H | Cl—[CF₃-phenyl-Cl]—O— (H) | H (Cl—[CF₃-phenyl-Cl₂]—O—) | H | CF₃ | m.p. 227° C. |
| II-3 | H | F (H) | H (F) | H | CF₃ | m.p. 213° C. |
| II-4 | H | NO₂ (H) | H (NO₂) | H | CF₃ | m.p. 151° C. |
| II-5 | H | Cl (H) | H (Cl) | H | CF₃ | m.p. 193° C. |
| II-6 | Cl (H) | H (Cl) | Cl (H) | H (Cl) | CF₃ | m.p. 165–170° C. |
| II-7 | Br | (Cl) | Cl | H | CF₃ | m.p. 195–149° C. |

\*)The ¹H-NMR spectra were recorded in deuterochloroform (CDCl₃) or hexadeutero-dimethyl sulphoxide (DMSO-d₆) using tetramethylsilane (TMS) as the internal standard. The value given is the chemical shift as d in ppm.

Chloro-(2-halogeno-1-fluoromethyl-ethoxy)-methanes of the formula

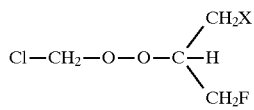

case optionally substituted alkyl, alkoxy, alkylthio, alkylsulphinyl, alkylsulphonyl or cycloalkyl, optionally substituted, fused-on dioxyalkylene, or represent hydroxycarbonyl, alkylcarbonyl, alkoxycarbonyl, cycloalkoxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but with at least one of the substituents $X^1$, $X^2$, $X^3$ or $X^4$ representing a halogenoalkyl with the exception of the chloromethyl radical, halogenoalkoxy, halogenoalkylthio, halogenoalkylsulphinyl, halogenoalkylsulphonyl, alkylsulphonyl, optionally substituted fused-on dioxyalkylene, hydroxycarbonyl, alkylcarbonyl, alkoxycarbonyl, cycloalkoxycarbonyl, in each case optionally substituted amino or aminocarbonyl or in each case optionally substituted aryl, arylthio, arylsulphinyl, arylsulphonyl, arylsulphonyloxy, arylcarbonyl, aryloxycarbonyl, arylazo or arylthiomethylsulphonyl,
from benzimidazoles of the formula

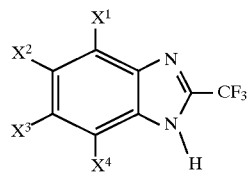

EXAMPLE 192 g of 1,3-difluoro-2-propanol were admixed with 66 g of paraformaldehyde (finely powdered). Then, at −10° C., a vigorous stream of hydrogen chloride gas was passed in with stirring until a clear 2-phase mixture had been formed. Subsequently the organic phase was separated off, dried with calcium chloride and subjected to fractional distillation in vacuo. 183 g (60% of theory) of chloro-(2-fluoro-1-fluoromethyl-ethoxy)-methane were obtained with a boiling point of 50° to 54° C. at 20 mbar. The characteristic absorptions in the NMR spectra were as follows:

$^1$H-NMR: 5.6 ppm and 4.55 ppm.

$^{19}$F-NMR: −233 ppm.

Fluorinated 1,3-benzo-dioxoles of the formula

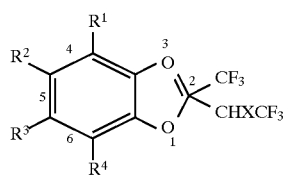

in which

X represents hydrogen, fluorine, chlorine or bromine, and $R^1$ and $R^4$ may be identical to or different from one another and in each case denote hydrogen, halogen, $C_1$–$C_6$-alkyl, $C_1$–$C_6$-alkoxy, halogeno-$C_1$–$C_6$-alkyl, $C_6$–$C_{10}$-aryl, COOH, CN, NCO, COO—$C_1$–$C_6$-alkyl, NH—$C_1$–$C_6$-alkyl, N($C_1$–$C_6$-alkyl)$_2$, and $R^2$ and $R^3$ represent $NO_2$ or $NH_2$, are obtainable by reacting 1,2-dihydroxybenzenes

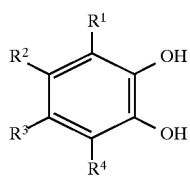

in which $R^1$ to $R^4$ have the meaning given above, but $R^1$ to $R^3$ do not represent OH, COCl or $SO_2Cl$, in the presence of a base and a diluent at −20° to +200° C. with a hexafluorobutene of the formula

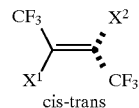

in which $X^1$ represents hydrogen or halogen and $X^2$ represents halogen, or by reacting 1,2-dihydroxybenzenes which are provided with a protective group and are of the formula

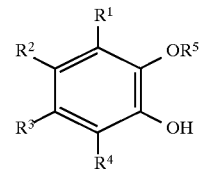

in which $R^1$ to $R^4$ have the meaning given above and $R^5$ represents a protective group or $R^5$, together with $R^1$, represents a —C(CH$_3$)$_2$—O— radical first with a hexafluorobutene of the formula

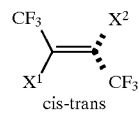

in which $X^1$ represents hydrogen or halogen and $X^2$ represents halogen, to obtain an intermediate of the formula

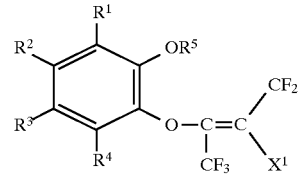

in which $X^1$ and $R^1$ to $R^5$ have the meaning given above, then eliminating the protective group $R^5$ from the intermediate of the above formula, and then reacting the OH compound thus obtainable with a base, to obtain 1,3-benzodioxoles of the above formula.

1,3-Benzo-dioxoles which contain two adjacent amino groups can be converted with trifluoroacetic acid into the corresponding benzimidazole, e.g. of the following formula

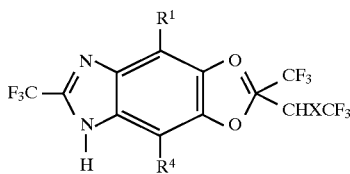

in which

R¹, R⁴ and X have the meaning given above.

From these compounds it is possible to obtain, by alkylation, benzimidazole derivatives which are substituted on the nitrogen atom with a

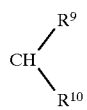

radical.

EXAMPLES

Example 1a 2-(2,2,2-Trifluoroethyl)-2-trifluoromethyl-1,3-benzodioxole 11 g of pyrocatechol were dissolved in 200 ml of dimethylformamide, and 18 g of 45% strength by weight aqueous sodium hydroxide solution were added. 20 g of 2-chloro-1,1,1,4,4,4-hexafluoro-2-butene were added dropwise at 75° C. to the mixture. Stirring was continued at 75° C. for 30 minutes. The mixture was then poured into 500 ml of ice-water and extracted with diethyl ether. The organic phase was washed with water, dried with magnesium sulphate and concentrated. Finally, the product was distilled under a high vacuum. The yield was 15 g (=56%) and the boiling point was 60° C. at 10 mbar. The NMR spectra showed the following characteristic absorptions: $^{19}$F-NMR: −59.0 and −84.6 ppm; $^1$H-NMR: 3.02 ppm.

Example 2a 2-(1-Chloro-2,2,2-trifluoroethyl)-2-trifluoromethyl-1,3-benzodioxole 110 g of pyrocatechol were dissolved in 1,500 ml of acetonitrile, and 200 g of triethylamine were added. 235 g of 2,3-dichloro-1,1,1,4,4,4-hexafluoro-2-butene were added dropwise at 75° C. to the mixture. Stirring was continued at 75° C. for 2 hours. 1,200 ml of the solvent were then distilled off in vacuo and the residue was taken up in 1,500 ml of water. The product was extracted with diethyl ether and the organic phase was washed twice with 10% strength by weight aqueous sodium hydroxide solution and once with water. After drying with magnesium sulphate the product was concentrated and subjected to fractional distillation in vacuo. The yield was 258 g (=84% of theory). The boiling point was 63° C. at 12 mbar. The NMR spectra showed the following characteristic absorptions: $^{19}$F-NMR: −66.8 and −79.7 ppm; $^1$H-NMR: 4.71 ppm.

Examples 3a 2-(1,1,1,4,4,4-Hexafluoro-2-butenoxy)-methoxybenzene 260 g of 2-methoxyphenol were dissolved in 1 l of dimethylformamide (technical grade), and 220 g of 45% sodium hydroxide solution were added. Then 400 g of 2-chloro-1,1,1,4,4,4-hexafluoro-2-butene were added dropwise with stirring at 22° C. Stirring was continued at 22° C. for 2 hours. Then 1.5 l of ice-water was added and the mixture was extracted with methylene chloride.

The combined organic phases were washed twice with 10% strength sodium hydroxide solution and once with saturated NaCl solution, dried with MgSO₄ and distilled. The yield was 329 g (58% of theory) and the boiling point was 68°–70° C. at 12 mbar. The NMR spectra showed the following characteristic absorptions: $^{19}$F-NMR: −57.6 and −67.9 ppm; $^1$H-NMR: 5.92 ppm.

Example 4a 2-(1,1,1,4,4,4-hexafluoro-2-butenoxy)-phenol 286.1 g of 2-(1,1,1,4,4,4-hexafluoro-2-butenoxy)-methoxybenzene from Example 3a were dissolved in a mixture of 500 ml of glacial acetic acid and 500 ml of 48% strength hydrobromic acid, and 5 g of triethylbenzylammonium chloride were added. The mixture was stirred at a bath temperature of 150° C. until, according to gaschromatographic monitoring, complete reaction had been achieved. The mixture was then allowed to cool, and 2 kg of ice-water were added. The aqueous phase was extracted thoroughly with CH₂Cl₂. After drying with MgSO₄ the solvent was stripped off and the residue was distilled in vacuo. The yield was 200 g (50% of theory) and the boiling point was 80° C. at 16 mbar. The NMR spectra showed the following characteristic absorptions: $^{19}$F-NMR: −59.6 and −69.6 ppm; $^1$H-NMR: 6.1 ppm.

Example 5a 2-(2,2,2-Trifluoroethyl)-2-trifluoromethyl-1,3-benzodioxole 200 g of 2-(1,1,1,4,4,4-hexafluoro-2-butenoxy)-phenol from Example 4a were dissolved in 400 ml of acetonitrile, and 5 g of triethylamine were added. The mixture was stirred at 70° C. for 4 h. Distillation was then carried out in vacuo. The yield was 162 g (81% of theory) and the boiling point was 60° C. at 10 mbar. The NMR spectra showed the following characteristic absorptions: $^{19}$F-NMR: −59.0 and −84.6 ppm; $^1$H-NMR: 3.02 ppm.

Example 6a 2-(2-Chloro-1,1,1,4,4,4-hexafluoro-2-butenoxy)-1-benzyloxybenzene 20 g of 2-benzyloxyphenol were dissolved in 100 ml of dimethylformamide, and 9 g of 45% strength sodium hydroxide solution were added. 23 g of 2,3-dichloro-1,1,1,4,4,4-hexafluoro-2-butene were then added dropwise at room temperature. After the exothermic reaction had subsided the mixture was stirred at room temperature for a further 1 hour and then added to water and extracted with tert-butyl methyl ether. The mixture was dried with MgSO₄ and the solvent was then stripped off. The yield was 29 g (74% of theory). The NMR spectra showed the following characteristic absorptions: $^{19}$F-NMR: −59.5, −60.5, −61.7 and −62.8 ppm.

Example 7a 2-(2-Chloro-1,1,1,4,4,4-hexafluoro-2-butenoxy)-phenol 24.4 g of 2-(2-chloro-1,1,1,4,4,4-hexafluoro-2-butenoxy)-1-benzyloxybenzene from Example 6a were dissolved in 150 ml of tetrahydrofuran and treated at room temperature for 4 hours with 3 bar of hydrogen in the presence of 2 g of Pd/C (10%). The mixture was then filtered and the filtrate concentrated and distilled in vacuo. The yield was 13.2 g (69% of theory) and the boiling point was 56° C. at 0.15 mbar.

Example 8a 2-(1-Chloro-2,2,2-trifluoroethyl)-2-trifluoromethyl-1,3-benzodioxole 11.7 g of 2-(2-chloro-1,1,1,4,4,4-hexafluoro-2-butenoxy)-phenol from Example 7a were dissolved in 40 ml of tert-butyl methyl ether, and 40 ml of 1N sodium hydroxide solution were added. After stirring at room temperature for 30 minutes, the organic phase was separated off, dried with $MgSO_4$ and distilled. The yield was 10 g (88% of theory) and the boiling point was 63° C. at 12 mbar. The NMR spectra showed the following characteristic absorptions: $^{19}$F-NMR: −66.8 and −79.7 ppm; $^1$H-NMR: 4.71 ppm.

Example 9a 2,2-Dimethyl-4-(1,1,1,4,4,4-hexafluoro-2-butenoxy)-1,3-benzodioxole (formula V, $R^5$ together with $R^1$=—$C(CH_3)_2$—O— radical)

46 g of 2,2-dimethyl-4-hydroxy-1,3-benzodioxole (formula IV, $R^5$ together with $R^3$=—$C(CH_3)_2$—O— radical) were dissolved in 200 ml of N-methylpyrrolidone, and 31 g of 40% strength by weight aqueous sodium hydroxide solution were added. 54.8 g of 2-chloro-1,1,1,4,4,4-hexafluoro-2-butene were then added dropwise while stirring at room temperature. After stirring further for 1 hour, the batch was poured into water and extracted with tert-butyl methyl ether. The organic phase was washed with 10% strength by weight aqueous sodium hydroxide solution and dried with magnesium sulphate, and the readily volatile fractions were removed on a rotary evaporator. There remained 73.8 g (=80% of theory) of a product which was 95% pure according to gas chromatography. The characteristic absorptions in the NMR spectra were: $^{19}$F-NMR: −58.1 and −68.5 ppm; $^1$H-NMR: 6.73, 6.55, 6.03 and 1.70 ppm.

Example 10a 1,2-Dihydroxy-3-(1,1,1,4,4,4-hexafluoro-2-butenoxy)-benzene 65 g of the product from Example 9a were heated to boiling, at reflux, with 200 ml of concentrated aqueous hydrochloric acid for 4 hours, while stirring. The mixture was then diluted with 300 ml of water and extracted with methylene chloride. After drying the extract with magnesium sulphate, the solvent was stripped off from the organic phase to give 54 g of a 90% pure product. Recrystallization from cyclohexane gave colourless crystals with a melting point of 105° C. The characteristic absorptions in the NMR spectra were as follows: $^{19}$F-NMR: −57.7 and −67.7 ppm; $^1$H-NMR: 6.77, 6.50, 6.21 and 5.42 ppm.

Example 11a 2-(2,2,2-Trifluoroethyl)-2-(trifluoromethyl)-4-hydroxy-1,3-benzodioxole (formula (I), $R^1$=OH, X=H, X=CH, $R^2$ and $R^3$=H)

43.5 g of the product from Example 10a were dissolved in 300 ml of acetonitrile, and 1.5 g of triethylamine was added at room temperature. After stirring at room temperature for 2 hours, the solvent was stripped off and the residue distilled in vacuo. The yield was 17 g (=39% of theory), the boiling point was 85° C. at 0.15 mbar, and the melting point was 65° C. The characteristic absorptions in the NMR spectra were as follows: $^{19}$F-NMR: −59.0 and −84.5 ppm; $^1$H-NMR: 6.80, 6.55, 6.2 and 3.01 ppm.

Example 12a 2,2-Dimethyl-4-(3-chloro-1,1,1,4,4,4-hexafluoro-2-butenoxy)-1,3-benzodioxole formula (V), $R^1$ and $R^5$ together are —$C(CH_3)_2$—O—, $X^1$=Cl, $R^2$+$R^3$=H, A=CH)

33.2 g of 2,2-dimethyl-4-hydroxy-1,3-benzodioxole were reacted in analogy to Example 9a with 47 g of 2,3-dichloro-1,1,1,4,4,4-hexafluoro-2-butene. The product obtained was distilled in vacuo, and a 1:1 molar mixture of cis/trans isomers was obtained. The yield was 51 g (=70% of theory) and the boiling point was 70° C. at 0.15 mbar. The characteristic absorptions in the NMR spectra were as follows: $^{19}$F-NMR: −60.0, −61.6, −62.2 and −63.4 ppm; $^1$H-NMR: 6.79, 6.65 to 6.48 and 1.7 ppm.

Example 13a 1,2-Dihydroxy-3-(3-chloro-1,1,1,4,4,4-hexafluoro-2-butenoxy)-benzene(formula(V),$R^1$=OH, $R^2$+$R^3$=H, A=CH, $R^5$=H, $X^1$=Cl)

18 g of the product from Example 12a were reacted in analogy to Example 10a with 50 ml of concentrated hydrochloric acid. 15.7 g of a 97% pure product were obtained. The product was a 1:1 molar mixture of the cis/trans isomers. The characteristic absorptions in the NMR spectra were as follows: $^{19}$F-NMR: −60.2, −61.3, −62.2 and −63.3 ppm; $^1$H-NMR: 6.80, 6.45 and 6.25 ppm.

Example 14a 2-(1-Chloro-2,2,2-trifluoroethyl)-2-trifluoromethyl-4-hydroxy-1,3-benzodioxole 15 g of the product from Example 13a were dissolved in 50 ml of acetonitrile, and 1 ml of triethylamine was added. After stirring for 15 minutes, the solvent was stripped off and the residue was distilled in vacuo. For purification the product was taken up in diethyl ether and filtered through silica. After stripping off the diethyl ether there remained 10.5 g of the product (=70% of theory). The melting point was 139° to 141° C. The characteristic absorptions in the NMR spectra were as follows: $^{19}$F-NMR: −66.6 and −79.3 ppm; $^1$H-NMR: 8.4, 6.76, 6.60, 6.50 and 4.70 ppm.

Example 15a

5-Nitro-2-(2,2,2-trifluoroethyl)-2-trifluoromethyl-1,3-benzodioxole

A solution of 54.4 g of 2-(2,2,2-trifluoroethyl)-2-trifluoromethyl-1,3-benzodioxole in 75 ml of methylene chloride was added dropwise at 10° C. to a mixture of 40 ml of 65% strength by weight nitric acid and 40 ml of concentrated sulphuric acid. The mixture was stirred at room temperature for a further 1 hour and then poured into ice-water, the organic phase was then separated off and the aqueous phase was extracted with methylene chloride. The combined organic phases were washed with water, dried, and freed from readily volatile constituents. There remained 95 g of the product (=86% of theory) with a melting point of 87° to 88° C.

The NMR spectra showed the following characteristic absorptions: $^{19}$F-NMR: −59.0 and −69.4 ppm; $^{1}$H-NMR: 3.10 ppm.

Example 16a

5-Nitro-2-(1-chloro-2,2,2-trifluoroethyl)-2-trifluoromethyl-1,3-benzodioxole 613 g of 2-(1-chloro-2,2,2-trifluoroethyl)-2-trifluoromethyl-1,3-benzodioxole from Example 2a were dissolved in 1.2 l of methylene chloride, and the solution was added dropwise at 0° to 10° C. to a mixture of 400 ml of 65% strength nitric acid and 400 ml of concentrated sulphuric acid. The mixture was stirred at room temperature for a further 2 hours. It was then added carefully to 2 l of ice-water and extracted with methylene chloride. The combined organic phases were washed 2 times with water, dried and concentrated. The yield was 652 g (93% of theory). The NMR spectra showed the following characteristic absorptions: $^{19}$F-NMR: −66.4 and −79.2 ppm; $^{1}$H-NMR: 4.81 ppm.

Example 17a 5,6-Dinitro-2-(2,2,2-trifluoroethyl)-2-trifluoromethyl-1,3-benzodioxole A mixture of 250 ml of 100% strength by weight nitric acid and 350 ml of concentrated sulphuric acid was added dropwise to an initial charge of 317 g of the product from Example 15a. The mixture was stirred at 55° C. for 2 hours. The mixture was then cooled and poured into ice-water. The product was extracted with methylene chloride, washed until neutral with sodium hydrogen carbonate solution, dried, and freed on a rotary evaporator from readily volatile constituents. The yield was 339 g (=94% of theory) and the melting point was 101° to 103° C.

The NMR spectra showed the following characteristic absorptions: $^{19}$F-NMR: −60.9 and −86.5 ppm; $^{1}$H-NMR: 3.18 ppm.

Example 18a 5,6-Dinitro-2-(1-chloro-2,2,2-trifluoroethyl)-2-trifluoromethyl-1,3-benzodioxole A mixture of 250 ml of 100% strength by weight nitric acid and 350 ml of concentrated sulphuric acid was added to an initial charge of 352 g of 5-nitro-2-(1-chloro-2,2,2-trifluoroethyl)-2-trifluoromethyl-1,3-benzodioxole from Example 16a. The mixture was stirred at 60° C. for 2 hours. It was cooled, poured into ice-water and extracted with methylene chloride. After washing the mixture with sodium hydrogen carbonate solution, and drying, it was concentrated on a rotary evaporator. The yield was 392 g (91% of theory) and the melting point was 125° C. The NMR spectra showed the following characteristic absorptions: $^{19}$F-NMR: −68.5 and −81.0 ppm; $^{1}$H-NMR: 4.86 ppm.

Example 19a

5-Amino-2-(2,2,2-trifluoroethyl)-2-trifluoromethyl-1,3-benzodioxole 57.4 g of the product from Example 15a were dissolved in 400 ml of tetrahydrofuran and hydrogenated with hydrogen in the presence of 4 g of catalyst (palladium on carbon, 10% by weight) at 30° C. for 5 hours and at 50 bar. The mixture was then filtered, the solvent removed, and the remaining filtrate distilled under a high vacuum. 37 g of product (=63% of theory) were obtained with a boiling point of 83° C. at 0.07 mbar. $^{19}$F-NMR: −59.0 and −84.6 ppm; $^{1}$H-NMR: 2.98 ppm.

Example 20a

5-Amino-2-(1-chloro-2,2,2-trifluoroethyl)-2-trifluoromethyl-1,3-benzodioxole 72 g of 5-nitro-2-(1-chloro-2,2,2-trifluoroethyl)-2-trifluoromethyl-1,3-benzodioxole from Example 16a were dissolved in 500 ml of tetrahydrofuran, and hydrogenated on 5 g of palladium on carbon (5%) at room temperature for 5 hours with 15 to 20 bar of hydrogen. The mixture was then filtered and the solvent stripped off in vacuo. The yield was 60 g (93% of theory) and the boiling point was 80° to 82° C. at 0.1 mbar. The NMR spectra showed the following characteristic absorptions: $^{19}$F-NMR: −66.5 and −79.4 ppm; $^{1}$H-NMR: 4.68 ppm.

Example 21a 5,6-Diamino-2-(2,2,2-trifluoroethyl)-2-trifluoromethyl-1,3-benzodioxole 339 g of the product from Example 17a were dissolved in 2,000 ml of tetrahydrofuran, and 20 g of catalyst (palladium on carbon, 5% by weight) were added. Hydrogenation was carried out with hydrogen at 25 to 30 bar and at room temperature for 13 hours. The mixture was then filtered and the solvent stripped off in vacuo. A solid remained. The yield was 274 g (=96% of theory). $^{19}$F-NMR: −61.2 and −86.6 ppm; $^{1}$H-NMR: 3.02 ppm.

Example 22a 2-(2,2,2-Trifluoroethyl)-2-trifluoromethyl-1,3-benzodioxole 306.5 g of 2-(1-chloro-2,2,2-trifluoroethyl)-2-trifluoromethyl-1,3-benzodioxole from Example 2a were dissolved in 500 ml of THF, and 101 g of triethylamine and 30 g of palladium on carbon (5% by weight) were added. Hydrogenation was then carried out with 100 bar of hydrogen at 110° C. for 48 h. The mixture was then filtered, the solvent stripped off in vacuo and the residue subjected to fractional distillation in vacuo. The yield was 126 g (46% of theory) and the boiling point was 60° C. at 10 mbar. The NMR spectra showed the following characteristic absorption: $^{19}$F-NMR: −59.0 and −84.6 ppm; $^{1}$H-NMR: 3.02 ppm.

o-Phenylenediamines containing fluoroalkyl(ene) groups and of the formula

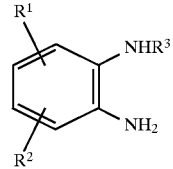

in which $R^1$ represents $CF_3$, $OCF_3$, $SCF_3$, $SO_2$—$C_1$–$C_6$-alkyl, which can be straight-chain or branched and may be substituted wholly or partially by fluorine, $N(CF_3)_2$, a phenyl or phenoxy radical with $CF_3$ or CN in the 4 position and optionally further substituents, 1,1,2,3,3,3-hexafluoropropoxy, 1,1,2-trifluoro-2-chloro-ethoxy, 1,1,2,2-tetrafluoroethoxy, 1,1,2-trifluoro-2-chloro-ethylthio or 1,1,2,3,3,3-hexafluoropropylthio, and, independently thereof, $R^2$ represents F, Cl, Br, CN, $CH_3$, $OCF_3$, $SO_2$—$C_1$–$C_6$-alkyl which can be straight-chain or branched and may be substituted wholly or partially by fluorine, COO—$C_1$–$C_6$-alkyl, $COOC_6H_5$, 1,1,2,2-tetrafluoroethoxy, 1,1,2,3,3,3-hexafluoropropoxy or 1,1,2-trifluoro-2-chloro-ethoxy, and $R^3$ represents hydrogen, $COCH_3$ or $COCF_3$, where $R^1$ and $R^2$ can together represent a —O—CFCl—CFCl—O— radical, with the exception of the compounds described in EP-A 251 013 and EP-A 487 286, are obtainable by dinitrating a benzene derivative of the formula

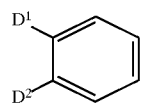

in which $D^1$ represents $CF_3O$, $CF_3S$, $CHF_2CF_2O$, $CHFCl$—$CF_2O$, $CF_3CHFCF_2O$, $CF_3CF_2O$, $CF_3CF_2CF_2O$, $CF_3CF_2S$ or $CF_3CHFCF_2O$, and $D^2$ represents $CF_3O$, $CF_3S$, $CHF_2CF_2O$, $CHFCl$—$CF_2O$, $CF_3CHF$—$CF_2O$, $CF_3CF_2O$, $CF_3CF_2CF_2O$, $CF_3CF_2S$ or $CF_3CHFCF_2O$, fluorine, chlorine, bromine, $C_1$–$C_6$-alkyl or $C_1$–$C_6$-alkoxy, and subsequently reducing the nitro groups to obtain compounds in which $R^1$ and $R^2$ are in the 4 and 5 positions with respect to the amino groups and have the meaning of $D^1$ and $D^2$.

If it is intended to prepare compounds in which $R^1$ has the meaning given above and is in the 4 position with respect to the amino groups, and $R^2$ represents Cl or Br and is in the 5 position with respect to the amino groups, then, for example, a nitrobenzene derivative of the formula

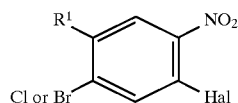

in which $R^1$ has the meaning given and

Hal represents fluorine, chlorine or bromine, can be reacted with ammonia, the Hal group thus being exchanged for an amino group, and the resulting nitroaniline can be reduced.

If it is intended to prepare compounds in which $R^1$ has the meaning given above and is in the 4 position with respect to the amino groups, $R^2$ represents chlorine or bromine and is in the 6 position with respect to the amino groups and $R^3$ denotes hydrogen, then, for example, a nitroaniline of the formula

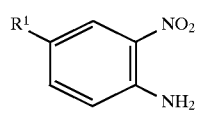

in which $R^1$ has the meaning given above can be reacted with a chlorinating or brominating agent, a chlorine or bromine atom thus being introduced into the position meta to the nitro group, and the nitro group can subsequently be reduced.

If it is intended to prepare compounds in which $R^1$ represents a donor group in the 4 position with respect to the two amino groups, $R^2$ represents an acceptor group, e.g. COO—$C_1$–$C_6$-alkyl, CN, $CF_3$ or $SO_2$—$C_1$–$C_6$-alkyl, and $R_3$ is not hydrogen, a benzene derivative of the formula

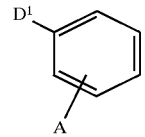

in which $D^1$ has the meaning given above and

A represents $CF_3$, $SO_2$—$C_1$–$C_6$-alkyl which is straight-chain or branched and may be substituted wholly or partially by fluorine, COO—$C_1$–$C_6$-alkyl or CN, for example, can then be mononitrated (introduction of the $NO_2$ group into the position para to $D^1$), the $NO_2$ group can be reduced to the $NH_2$ group, the $NH_2$ group can be acylated with, for example, acetic acid or trifluoroacetic acid, the product can again be mononitrated (introduction of this $NO_2$ group into the position ortho to the NHCOR group where R=e.g. $CH_3$ or $CF_3$), this $NO_2$ group can be reduced to the $NH_2$ group and, optionally, if it is desired to prepare a compound of the above formula where $R^3$=hydrogen, the acyl group can be eliminated by hydrolysis.

The o-phenylenediamines containing fluoroalkyl(ene) groups, in which $R^3$ denotes hydrogen, can initially be reacted with trifluoroacetic acid to give 2-trifluoromethylbenzimidazoles of the formula

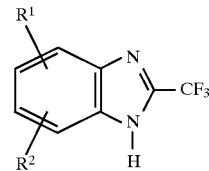

and then further reacted with compounds of the formula

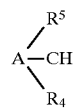

where $R^1$ and $R^2$ adopt the above scope of meaning, $R^4$ represents hydrogen, alkyl, alkoxy or optionally substituted aryl, $R^5$ represents hydroxyl, cyano or in each case optionally substituted alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy, and A denotes a suitable leaving group.

Leaving groups are known to those skilled in the art and are, for example, halogen, alkyl(alkoxy, aryl)sulphonyloxy, hydroxyl or alkoxy.

EXAMPLES

Examples 1 to 6b
(Dinitration and reduction)

Example 1b 320 g of 1,2-bis-(2-chloro-1,1,2-trifluoroethoxy)-benzene were added dropwise to 500 g of a mixed acid containing 33% by weight of $HNO_3$ and 67% by weight of $H_2SO_4$. After one hour at 40° C., 250 ml of 20% strength by weight oleum were added dropwise. The mixture was then heated to 80° C. and stirred for 15 hours. Subsequently a further 120 ml of 20% strength by weight oleum and 250 g of the abovementioned mixed acid were added dropwise. After 6 hours at 80° to 82° C., the mixture was cooled and poured onto ice. The organic phase was separated off and washed with water. After azeotropic drying with 1,2-dichloroethane, 350 g of 96% by weight pure 1,2-dinitro-4,5-bis-(2-chloro-1,1,2-trifluoroethoxy)-benzene were obtained (oil, $n_D^{20}$: 1.4832, GC 99.1%).

350 g of this dinitro compound were added dropwise to a mixture of 1.5 l of ethanol, 50 ml of water, 30 ml of concentrated aqueous hydrochloric acid and 470 g of iron filings, and heated to boiling at reflux for a total of 15 hours. The solution was subsequently cooled and then filtered, the filtrate concentrated, and the residue recrystallized from cyclohexane. 216 g of 1,2-diamino-4,5-bis-(2-chloro-1,1,2-trifluoroethoxy)-benzene having a melting point of 58° to 60° C. were obtained.

Example 2b

In analogy to Example 1, the corresponding 4,5-dinitro compound (oil, $n_D^{20}$: 1.4852) and the corresponding 4,5-diamino compound (oil, 87% by weight pure) were prepared from 1,2-bis-(1,1,2,3,3,3-hexafluoropropoxy)-benzene.

Example 3b

In analogy to Example 1, the corresponding 4,5-dinitro compound (melting point 56° to 57° C.) and the corresponding 4,5-diamino compound (melting point 67° to 68° C.) were prepared from 1-(1,1,2-trifluoro-2-chloroethoxy)-2-chlorobenzene.

Example 4b

In analogy to Example 1, the corresponding 4,5-dinitro compound (melting point 73° to 75° C.) and the corresponding 4,5-diamino compound (oil, 98% by weight pure, $n_D^{20}$: 1.5485) were prepared from 1-trifluoromethoxy-2-bromobenzene.

Example 5b

In analogy to Example 1, the corresponding 4,5-dinitro compound (melting point 55° to 56° C.) and the corresponding 4,5-diamino compound (melting point 56°–57° C.) were prepared from 1-trifluoromethoxy-2-chlorobenzene.

Example 6b

The corresponding 4,5-dinitro compound (oil) and the corresponding 4,5-diamino compound (oil) were prepared from 1-(1,1,2,3,3,3-hexafluoropropoxy)-2-chlorobenzene.

Examples 7 to 12b

Pressurization with ammonia and reduction

Example 7b 260 g of 3-nitro-2,5-dichlorobenzotrifluoride, 130 ml of water and 10 g of tetraethylammonium chloride were initially introduced into an autoclave, and 120 ml of liquid ammonia were injected. The mixture was then heated to 130° C. and stirred for 10 hours at this temperature. The mixture was cooled and then filtered, and the precipitate which was separated off was washed with water and dried. 194 g of 2-amino-3-nitro-5-chloro-benzotrifluoride with a melting point of 67° C. resulted.

134 g of the nitroaniline obtained as described above were dissolved in 800 ml of ethanol, and then 20 ml of water, 10 ml of concentrated aqueous hydrochloric acid and 160 g of iron filings were added. The mixture was heated for 15 hours to boiling at reflux, then cooled and filtered with suction and the filter residue washed with dichloromethane; the organic phases were subsequently freed from the solvent under reduced pressure. 171 g of 5-chloro-3-trifluoromethyl-1,2-diaminobenzene with a melting point of 53° C. resulted.

Example 8b

In analogy to Example 7, first 3-nitro-4-amino-6-chloro-difluorochloromethoxybenzene (melting point 73° C.) and from this 3,4-diamino-6-chloro-difluorochloromethoxy-benzene (oil) were obtained from 3-nitro-4,6-dichloro-difluorochloromethoxybenzene.

Example 9b

In analogy to Example 7, first 3-bromo-5-nitro-6-amino-benzotrifluoride (melting point 80° to 82° C.) and from this 3-bromo-5,6-diamino-benzotrifluoride (melting point 52° to 54° C.) were prepared from 3-bromo-5-nitro-6-chlorobenzotrifluoride.

Example 10b

In analogy to Example 7, first 3-cyano-4-amino-5-nitro-benzotrifluoride (melting point 99° to 100° C.) and from this 3-cyano-4,5-diamino-benzotrifluoride were prepared from 3-cyano-4-chloro-5-nitro-benzotrifluoride.

Example 11b

In analogy to Example 7, first 3-chloro-5-nitro-6-amino-benzotrifluoride (melting point 53° to 54° C.) and from this 3-chloro-5,6-diamino-benzotrifluoride were prepared from 3,6-dichloro-5-nitro-benzotrifluoride.

Example 12b

First 2-bromo-4-amino-5-nitro-(1,1,2-trifluoro-2-chloro-ethoxy)-benzene (melting point 90° C.) and from this 2-bromo-4,5-diamino-(1,1,2-trifluoro-2-chloro)-ethoxybenzene were prepared from 2-bromo-4-fluoro-5-nitro-(1,1,2-trifluoro-2-chloro)-ethoxybenzene.

Example 13b
(Halogenation of a nitroaniline and reduction)

24 g of finely powdered 2-nitro-4-trifluoromethylmercaptoaniline were dissolved in 50 ml of trifluoroacetic acid, and 18 g of bromine were metered in at 20° C. The mixture was then stirred at 20° C. for 3 hours and at 40° C. for a further 30 minutes. The mixture was added to water and the product was taken up in dichloromethane. Following removal of the solvent, 31 g of 6-bromo-2-nitro-4-trifluoromethyl-mercaptoaniline resulted.

155 g of the nitroaniline thus prepared were heated to boiling at reflux for 15 hours in 700 ml of ethanol together with 15 ml of water, 10 ml of concentrated aqueous hydrochloric acid and 70 g of iron filings; the mixture was then filtered, the filtrate freed from solvent under reduced pressure, and the crude solid product recrystallized from cyclohexane. 112 g of 6-bromo-4-trifluoromethyl-mercapto-1,2-diaminobenzene with a melting point of 60° to 61° C. were obtained.

Example 14b

In analogy to Example 13, 27 g of 2-nitro-4-trifluoromethyl-sulphonylaniline in 100 ml of acetic acid were brominated with 18 g of bromine.

After work-up, 32 g of 2-nitro-6-bromo-4-trifluoromethylsulphonyl-aniline resulted: melting point 147° C.

32 g of the nitroamine thus prepared were reduced with iron filings in alcohol and aqueous hydrochloric acid. 24 g of 3-bromo-5-trifluoromethylsulphonyl-phenylene-1,2-diamine resulted; melting point 155°–157° C.

Example 15b

In analogy to Example 14, 27 g of 2-nitro-4-trifluoromethylsulphonyl-aniline in 100 ml of acetic acid were chlorinated with 10 g of chlorine. 29 g of 2-nitro-4-trifluoromethylsulphonyl-6-chloro-aniline resulted; melting point 138°–139° C.

13 g of 3-chloro-5-trifluoromethylsulphonyl-1,2-phenylenediamine (melting point: 143°–145° C.) were obtained by reduction.

Example 16 to 20b
(Nitration and reduction in 2 stages)

Example 16b 263 g of 4-(2,6-dichloro-4-trifluoromethyl)-phenoxyacetanilide were dissolved in 1,100 ml of dichloromethane, and taken as initial charge at 10° C. 88 g of 98% strength by weight nitric acid were then added dropwise at this temperature. The mixture was subsequently stirred at 10° C. for 1 hour and at 30° C. for 2 further hours. After the addition of 300 ml of water, the phases were separated and the organic phase was freed from dichloromethane under reduced pressure. There remained 253 g of 2-nitro-4-(2,6-dichloro-4-trifluoromethyl-phenoxy)acetanilide with a melting point of 138°–140° C.

91 g of the acetanilide thus prepared were dissolved in 800 ml of dioxane, 10 g of Raney nickel were added, and hydrogenation was carried out at 25° to 45° C. in a hydrogenation apparatus with a maximum of 50 bar hydrogen pressure. The apparatus was let down, the mixture was filtered, and the dioxane was distilled off under a slight vacuum. There remained 65 g of 2-amino-4-(2,6-dichloro-4-trifluoromethyl-phenoxy)-acetanilide with a melting point of 222°–223° C.

Example 17b

In analogy to Example 16, first 3-trifluoromethyl-4-methoxy-6-nitro-acetanilide (melting point 143°–144° C.) and from this 3-trifluoromethyl-4-methoxy-6-amino-acetanilide (melting point 164°–165° C.) were prepared from 3-trifluoromethyl-4-methoxy-acetanilide.

Example 18b

In analogy to Example 16, first 3-trifluoromethyl-4-fluoro-6-nitro-trifluoromethylacetanilide (melting point 78° C.) and from this 3-trifluoromethyl-4-fluoro-6-amino-trifluoromethylacetanilide (melting point 92°–93° C.) were prepared from 3-trifluoromethyl-4-fluoro-trifluoromethylacetanilide.

Example 19b

In analogy to Example 16, first 3-trifluoromethyl-4-bromo-6-nitro-trifluoromethylacetanilide (melting point 110°–112° C.) and from this 3-trifluoromethyl-4-bromo-6-amino-trifluoromethylacetanilide (melting point 63°–65° C.) were prepared from 3-trifluoromethyl-4-bromo-trifluoromethylacetanilide.

Example 20b

In analogy to Example 16, first 3-trifluoromethylthio-4-chloro-6-nitro-trifluoromethylacetanilide (melting point 99°–100° C.) and from this 3-trifluoromethylthio-4-chloro-6-amino-trifluoromethylacetanilide (melting point 88°–90° C.) were prepared from 3-trifluoromethylthio-4-chloro-trifluoromethylacetanilide.

Example 21b 0.2 mol of 3-bromo-5-trifluoromethyl-phenylene-diamine were heated with 150 ml of trifluoroacetic acid at reflux temperature for 3 hours. For working up, excess trifluoroacetic acid was distilled off and the residue was partitioned between 100 ml of water and 300 ml of ethyl acetate. The organic phase was separated off, washed successively with in each case 100 ml of aqueous sodium hydrogen carbonate solution and water, dried over sodium sulphate, and concentrated in vacuo. The residue was purified by chromatography on silica gel (eluent: cyclohexane/ethyl acetate 1:1).

4-Bromo-6-trifluoromethyl-2-trifluoromethyl-1H-benzimidazole with a melting point of 149°–151° C. was obtained.

Example 22b 0.03 mol of 4-bromo-6-trifluoromethyl-2-trifluoromethyl-1H-benzimidazole and 0.06 mol of powdered potassium carbonate were heated in 70 ml of ethyl acetate at reflux temperature for 15 minutes; 3.9 g (0.04 mol) of chloromethyl methyl thioether in 20 ml of ethyl acetate were then added, and the mixture was heated with stirring at reflux temperature for a further 4 hours. For working up, the reaction mixture was cooled and then washed twice with in each case 40 ml of water, dried over sodium sulphate and concentrated in vacuo, and the residue was purified by chromatography on silica gel (eluent:dichloromethane).

1-Methylthiomethyl-4-bromo-6-trifluoromethyl-2-trifluoromethyl-benzimidazole with a melting point of 56°–60° C. was obtained.

USE EXAMPLES

In the Use Examples which follow, the compounds listed below were employed as comparison substances:

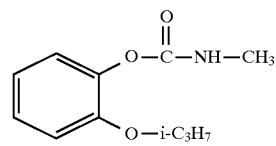
(A)

N-Methyl-O-(2-isopropoxyphenyl)-carbamate (cf. e.g. DE 11 08 202)

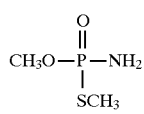

O,S-Dimethyl-thiolo-phosphoric acid amide (cf. e.g. DE 12 10 835)

Example A:

Phaedon larvae test:

Solvent: 7 parts by weight of dimethylformamide

Emulsifier: 1 part by weight of alkylaryl polyglycol ether

To produce a suitable preparation of active substance, 1 part by weight of active substance is mixed with the stated amount of solvent and the stated amount of emulsifier, and the concentrate is diluted with water to the desired concentration.

Cabbage leaves (*Brassica oleracea*) are treated by being dipped into the preparation of the active substance of the desired concentration and are infested with mustard beetle larvae (*Phaedon cochleariae*), as long as the leaves are still moist.

After the desired time, the destruction in percent is determined. 100% means that all the beetle larvae have been killed; 0% means that none of the beetle larvae has been killed.

In this test the following compound, for example, from the Preparation Examples exhibits superior activity over the prior art: 7.

TABLE A

*Phaedon larvae* test

| Active substances | Concentration of active substance in % | Degree of destruction in % after 3 days |
|---|---|---|
| (A) [known carbamate structure] | 0.1<br>0.01<br>0.001 | 100<br>70<br>0 |
| (7) [benzimidazole structure] | 0.1<br>0.01<br>0.001 | 100<br>100<br>100 |

Example B

Plutella test

Solvent: 7 parts by weight of dimethylformamide

Emulsifier: 1 part by weight of alkylaryl polyglycol ether

To produce a suitable preparation of active substance, 1 part by weight of active substance is mixed with the stated amount of solvent and the stated amount of emulsifier, and the concentrate is diluted with water to the desired concentration.

Cabbage leaves (*Brassica oleracea*) are treated by being dipped into the preparation of active substance of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars has been killed.

In this test the following compound, for example, from the Preparation Examples exhibits superior activity over the prior art: 1 and 7.

TABLE B

Plutella test

| Active substances | Concentration of active substance in % | Degree of destruction in % after 3 days |
|---|---|---|
| (A) [known carbamate structure] | 0.1<br>0.01<br>0.001 | 100<br>100<br>10 |
| (1) [benzimidazole structure] | 0.1<br>0.01<br>0.001 | 100<br>100<br>100 |
| (7) [benzimidazole structure] | 0.1<br>0.01<br>0.001 | 100<br>100<br>100 |

Example C

Heliothis virescens test

Solvent: 7 parts by weight of dimethylformamide

Emulsifier: 1 part by weight of alkylaryl polyglycol ether

To produce a suitable preparation of active substance, 1 part by weight of active substance is mixed with the stated amount of solvent and the stated amount of emulsifier, and the concentrate is diluted with water to the desired concentration.

Soya shoots (*Glycine max*) are treated by being dipped into the preparation of active substance of the desired concentration and are infested with the tobacco bud worm (*Heliothis virescens*) while the leaves are still moist.

After the desired time, the destruction in percent is determined. 100% means that all the caterpillars have been killed; 0% means that none of the caterpillars has been killed.

In this test the following compounds, for example, from the Preparation Examples exhibit superior activity over the prior art: 1, 2, 6, 7, 9, 18, 22 and 27.

TABLE C

*Heliothis virescens* test

| Active substances | | Concentration of active substance in % | Degree of destruction in % after 3 days |
|---|---|---|---|
| 2-isopropoxyphenyl N-methylcarbamate (known) | (A) | 0.1 | 10 |
| 5,6-dichloro-2-CF₃-1-(CH₂-O-C₂H₅)-benzimidazole | (1) | 0.1 | 100 |
| 5,6-dichloro-2-CF₃-1-(CH₂-N(CH₃)-C(O)-OCH₃)-benzimidazole | (2) | 0.1 | 100 |
| 5,6-dichloro-2-CF₃-1-(CH₂-N(n-C₃H₇)-C(O)-OCH₃)-benzimidazole | (6) | 0.1 | 100 |
| 4,6-dichloro-2-CF₃-1-(CH₂-OC₂H₅)-benzimidazole | (7) | 0.1 | 100 |
| 5,7-dichloro-2-CF₃-1-(CH₂-OC₂H₅)-benzimidazole | | | |
| 6-chloro-2-CF₃-1-(CH₂-O-i-C₃H₇)-benzimidazole | (9) | 0.1 | 100 |
| 5-chloro-2-CF₃-1-(CH₂-O-i-C₃H₇)-benzimidazole | | | |

TABLE C-continued

Heliothis virescens test

| Active substances | Concentration of active substance in % | Degree of destruction in % after 3 days |
|---|---|---|
| (18) | 0.1 | 100 |
| (22) | 0.1 | 100 |
| (27) | 0.1 | 100 |

Example D

Tetranychus test (OP-resistant)

Solvent: 7 parts by weight of dimethylformamide

Emulsifier: 1 part by weight of alkylaryl polyglycol ether

To produce a suitable preparation of active substance, 1 part by weight of active substance is mixed with the stated amount of solvent and the stated amount of emulsifier, and the concentrate is diluted with emulsifier-containing water to the desired concentrations.

Bean plants (*Phaseolus vulgaris*) which are heavily infested with all developmental stages of the red spider mite (*Tetranychus urticae*) are dipped in a preparation of the active substance of the desired concentration.

After the desired time, the destruction in percent is determined. 100% means that all the spider mites have been killed; 0% means that none of the spider mites has been killed.

In this test the following compounds, for example, from the Preparation Examples exhibit superior activity over the prior art: 8, 21, 22, 23, 24 and 25.

TABLE D
Tetranychus test (OP-resistant)
| Active substances | | Concentration of active substance in % | Degree of destruction in % after 7 days |
|---|---|---|---|
| 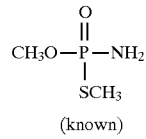 (known) | (B) | 0.01 | 60 |
| 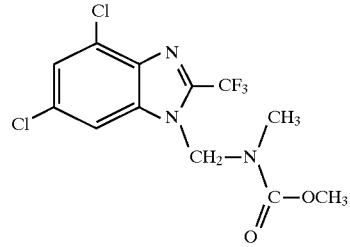 | (8) | 0.01 | 100 |
| 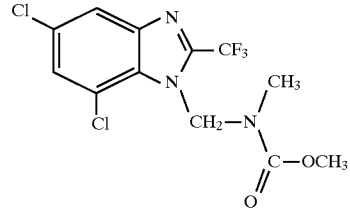 | | | |
| 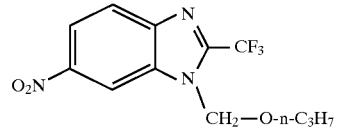 | (21) | 0.01 | 98 |
| 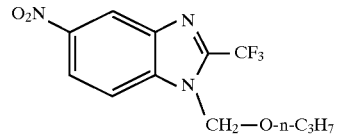 | | | |
| 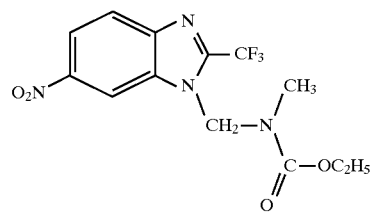 | (22) | 0.01 | 100 |
| 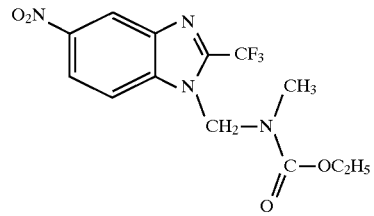 | | | |

TABLE D-continued

Tetranychus test (OP-resistant)

| Active substances | Concentration of active substance in % | Degree of destruction in % after 7 days |
|---|---|---|
| [structure: 5-nitro-2-trifluoromethyl-benzimidazole with N-CH₂-N(C₂H₅)(C(=O)-OC₂H₅)] | (23) 0.01 | 100 |
| [structure: 5-nitro-2-trifluoromethyl-benzimidazole (isomer) with N-CH₂-N(C₂H₅)(C(=O)-OC₂H₅)] | | |
| [structure: 5-nitro-2-trifluoromethyl-benzimidazole with N-CH₂-N(n-C₃H₇)(C(=O)-OC₂H₅)] | (24) 0.01 | 100 |
| [structure: 5-nitro-2-trifluoromethyl-benzimidazole (isomer) with N-CH₂-N(n-C₃H₇)(C(=O)-OC₂H₅)] | | |
| [structure: 5-nitro-2-trifluoromethyl-benzimidazole with N-CH₂-OH] | (25) 0.01 | 98 |
| [structure: 5-nitro-2-trifluoromethyl-benzimidazole (isomer) with N-CH₂-OH] | | |

Example E

Nematodes: Critical concentration test
Test nematode: Globodera rostochiensis
Solvent: 31 parts by weight of acetone
Emulsifier: 1 part by weight of alkylaryl polyglycol ether To produce a suitable preparation of active substance, 1 part by weight of active substance is mixed with the stated amount of solvent, the stated amount of emulsifier is added and the concentrate is diluted with water to the desired concentration.

The preparation of active substance is intimately mixed with the soil which is heavily contaminated with the test nematodes. The concentration of the active substance in the preparation is of practically no importance here, only the amount by weight of active substance per unit volume of soil, which is given in ppm (=mg/l), being decisive. The treated soil is transferred into pots, potatoes are planted in it, and the pots are maintained at a greenhouse temperature of 20° C.

After six weeks the potato roots are examined for cysts and the degree of effectiveness of the active substance is determined in %. The degree of effectiveness is 100% if infestation has been totally avoided, and is 0% if infestation is just as high as in the control plants in soil which is untreated but contaminated in the same way.

In this test the following compound, for example, from the Preparation Examples exhibits superior activity over the prior art: 1 and 7.

TABLE E

Nematodes test (*Globodera rostochiensis*)

| Active substances | | Degree of destruction in % | at an active substance concentration of 20 ppm |
|---|---|---|---|
| 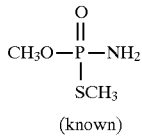 (known) | (B) | | 0 |
| 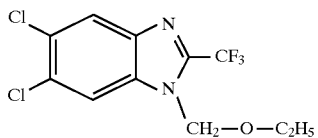 | (1) | | 100 |
| 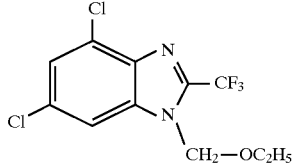 | (7) | | 100 |
| 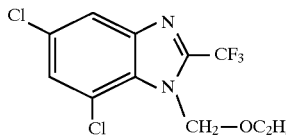 | | | |

Example F

Psoroptes ovis test:

Solvent: 35 parts by weight of ethylene glycol monomethyl ether

Emulsifier: 35 parts by weight of nonylphenol polyglycol ether

To produce a suitable preparation of active substance, 3 parts by weight of active substance are mixed with 7 parts of the solvent/emulsifier mixture indicated above, and the emulsion concentrate thus obtained is diluted with water to the desired concentration.

1 ml of this active substance preparation is pipetted into suitably sized PP blister packs. About 25 mites are then transferred into the active substance preparation.

After 24 hours the effectiveness of the active substance preparation is determined in %. 100% means that all the mites have been killed; 0% means that none of the mites has been killed.

In this test, the following compounds, for example, of the Preparation Examples display superior action compared to the prior art: 3, 4, 5 and 18.

TABLE F

Psoroptes ovis test

| Active substances | | Concentration of active substance in ppm of a.i. | Degree of destruction in % |
|---|---|---|---|
| 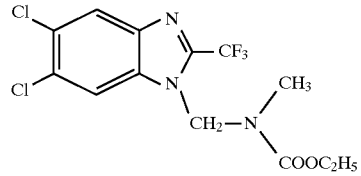 | (3) | 10 | 100 |

TABLE F-continued

Psoroptes ovis test

| Active substances | | Concentration of active substance in ppm of a.i. | Degree of destruction in % |
|---|---|---|---|
| 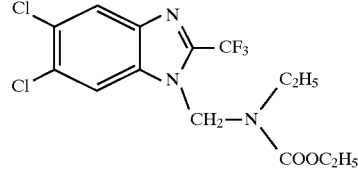 | (4) | 10 | 100 |
| 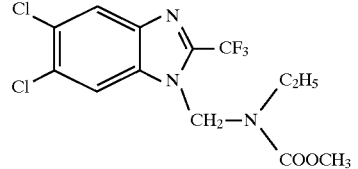 | (5) | 10 | 100 |
| 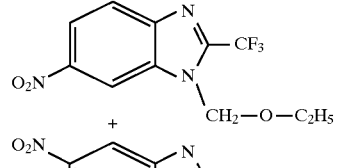<br>+<br>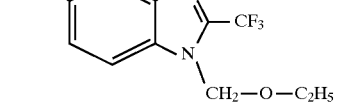 | (18) | 10 | 100 |

Example G

Periplaneta americana test:

Solvent: 35 parts by weight of ethylene glycol monomethyl ether

Emulsifier: 35 parts by weight of nonylphenol polyglycol ether

To produce a suitable preparation of active substance, 3 parts by weight of active substance are mixed with 7 parts of the abovementioned solvent/emulsifier mixture, and the resulting emulsion concentrate is diluted with water to the desired concentration.

2 ml of this active substance preparation are pipetted onto filter paper discs (diameter: 9.5 cm) which are located in suitably sized Petri dishes. After drying the filter discs, five cockroaches (*Periplaneta americana*) are transferred to the Petri dishes and covered.

After 3 days the effectiveness of the active substance preparation is determined in %. 100% means that all the cockroaches have been killed; 0% means that none of the cockroaches has been killed.

In this test the following compounds, for example, from the Preparation Examples exhibit superior activity over the prior art: 7, 8, 18, 19, 20 and 25.

TABLE G
*Periplanta americana* test
| Active substances | | Concentration of active substance in ppm of a.i. | Degree of destruction in % |
|---|---|---|---|
| 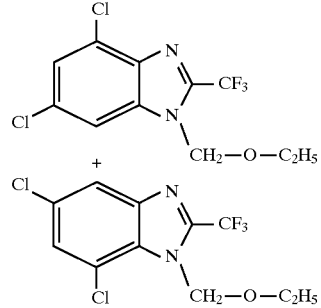 | (7) | 1000<br>100 | 100<br>100 |
| 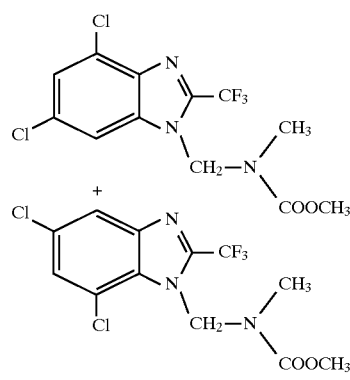 | (8) | 1000<br>100 | 100<br>100 |
| 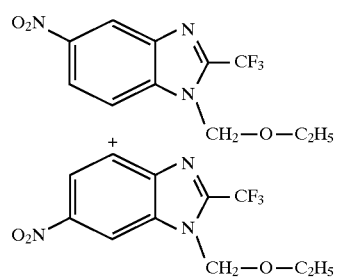 | (18) | 1000 | 100 |
| 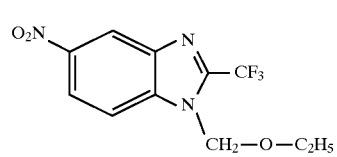 | (19) | 1000 | 100 |
| 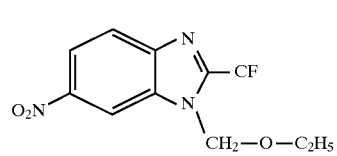 | (20) | 1000 | 100 |

TABLE G-continued

Periplanta americana test

| Active substances | | Concentration of active substance in ppm of a.i. | Degree of destruction in % |
|---|---|---|---|
| 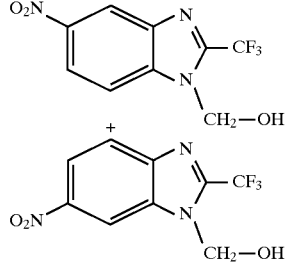 | (25) | 1000 | 100 |

Example H

Musca domestica test:

Solvent: 35 parts by weight of ethylene glycol monomethyl ether

Emulsifier: 35 parts by weight of nonylphenol polyglycol ether

To produce a suitable preparation of active substance, 3 parts by weight of active substance are mixed with 7 parts of the abovementioned solvent/emulsifier mixture, and the resulting emulsion concentrate is diluted with water to the desired concentration.

2 ml of this active substance preparation are pipetted onto filter paper discs (diameter: 9.5 cm) which are located in suitably sized Petri dishes. After drying the filter discs, 25 test organisms (*Musca domestica*; strain WHO [N]) are transferred to the Petri dishes and covered.

After 3 days the effectiveness of the active substance preparation is determined in %. 100% means that all the flies have been killed; 0% means that none of the flies has been killed.

In this test the following compounds, for example, from the Preparation Examples exhibit superior activity over the prior art: 7, 11, 18, 19, 20 and 25.

TABLE H

Musca domestica test

| Active substances | | Concentration of active substance in ppm of a.i. | Degree of destruction in % |
|---|---|---|---|
| 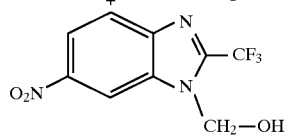 | (7) | 1000<br>100 | 100<br>>50 |
| 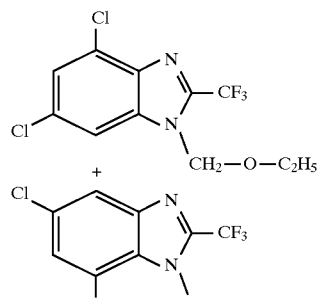 | (11) | 1000 | 100 |

TABLE H-continued

*Musca domestica* test

| Active substances | | Concentration of active substance in ppm of a.i. | Degree of destruction in % |
|---|---|---|---|
| (structure: 5-nitro-2-CF₃-1-(CH₂-O-C₂H₅)-benzimidazole + 6-nitro isomer) | (18) | 1000<br>100 | 100<br>>50 |
| (structure: 5-nitro-2-CF₃-1-(CH₂-O-C₂H₅)-benzimidazole) | (19) | 1000<br>100 | 100<br>100 |
| (structure: 6-nitro-2-CF₃-1-(CH₂-O-C₂H₅)-benzimidazole) | (20) | 1000<br>100 | 100<br>>50 |
| (structure: 5-nitro-2-CF₃-1-(CH₂-OH)-benzimidazole + 6-nitro isomer) | (25) | 1000 | 100 |

We claim:

1. A benzimidazole of the formula

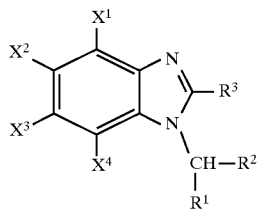

(I)

in which

R¹ represents hydrogen,

R² represents alkoxy having 1 to 8 carbon atoms or amino, optionally substituted with $C_1$–$C_8$-alkyl, $C_1$–$C_8$-alkoxycarbonyl or both, R³ represents perhalogenoalkyl having 1 to 8 carbon atoms, and X¹ represents hydrogen or halogen, X² represents hydrogen, halogen or nitro, X³ represents hydrogen, halogen or nitro, X⁴ represents hydrogen, but with at least one of the substituents X¹, X² X³ or X⁴ being different from hydrogen, with the exception of the compound 1-cyanomethyl-2-trifluoromethyl-5,6-dichlorobenzimidazole.

2. A composition for combating arthropods or nematodes comprising an amount effective therefore of a substituted benzimidazole of the formula (I) according to claim 1 and an inert solvent or carrier.

3. A process for combating pests selected from the group consisting of arthropods and nematodes which comprises applying to said pests or to a habitat of said pests an amount effective therefor of a benzimidazole of the formula (I) according to claim 1.

* * * * *